United States Patent
Keller et al.

(10) Patent No.: US 9,652,674 B2
(45) Date of Patent: May 16, 2017

(54) ICE ANALYSIS BASED ON ACTIVE AND PASSIVE RADAR IMAGES

(71) Applicant: The Johns Hopkins University, Baltimore, MD (US)

(72) Inventors: Mary R. Keller, Silver Spring, MD (US); Christopher M. Gifford, Laurel, MD (US); William C. Walton, Severn, MD (US); Nathaniel S. Winstead, Catonsville, MD (US)

(73) Assignee: The Johns Hopkins University, Baltimore, MD (US)

( * ) Notice: Subject to any disclaimer, the term of this patent is extended or adjusted under 35 U.S.C. 154(b) by 83 days.

(21) Appl. No.: 14/926,339

(22) Filed: Oct. 29, 2015

(65) Prior Publication Data
US 2016/0125586 A1 May 5, 2016

Related U.S. Application Data

(60) Provisional application No. 62/074,114, filed on Nov. 3, 2014.

(51) Int. Cl.
*G06K 9/00* (2006.01)
*G01S 13/89* (2006.01)
(Continued)

(52) U.S. Cl.
CPC ........... *G06K 9/0063* (2013.01); *G01S 7/024* (2013.01); *G01S 7/411* (2013.01); *G01S 13/86* (2013.01); *G01S 13/89* (2013.01); *G01S 13/955* (2013.01); *G06T 7/11* (2017.01); *G06T 7/174* (2017.01); *G06T 2207/10044* (2013.01); *G06T 2207/20004* (2013.01); *G06T 2207/30192* (2013.01)

(58) Field of Classification Search
CPC ... B63B 2211/06; G01S 13/862; G01S 13/90; G01S 15/88; G01S 13/0209; G01S 7/411; G01S 13/86; G01S 13/955; G06K 9/0063; G06T 2207/10044; G06T 2207/20221
See application file for complete search history.

(56) References Cited

U.S. PATENT DOCUMENTS 3,665,466 A   5/1972 Hibbard
4,160,251 A * 7/1979 Lazarchik ............ G01K 11/006
                                            342/16

(Continued)

OTHER PUBLICATIONS

Sandven, Stein et al., "Sea Ice Monitoring by Remote Sensing," Book Chapter 8 [from Remote Sensing of the Marine Environment, Manual of Remote Sensing, Edition: Third Edition, vol. 6, Chapter: 8, Publisher: American Society for Photogrammetry and Remote Sensing, Maryland, USA, Editors: J. Gower, pp. 241-283], Jan. 2006, pp. 1-43.

*Primary Examiner* — Jingge Wu
(74) *Attorney, Agent, or Firm* — Noah J. Hayward

(57) ABSTRACT

An ice analyzer includes processing circuitry configured to receive a radiometer image including a geographic area including ice, receive a radar image including at least a portion of the geographic area, perform ice/water discrimination of the radiometer image and the radar image, generate a passive ice/water mask and an active ice/water mask based on the ice/water discrimination, merge the passive ice/water mask and the active ice/water mask into a typing mask, and type the ice based on the typing mask.

20 Claims, 29 Drawing Sheets

(51) Int. Cl.
  *G01S 7/02* (2006.01)
  *G01S 7/41* (2006.01)
  *G01S 13/86* (2006.01)
  *G01S 13/95* (2006.01)
  *G06T 7/11* (2017.01)
  *G06T 7/174* (2017.01)

(56) References Cited

U.S. PATENT DOCUMENTS

| | | | |
|---|---|---|---|
| 5,777,481 A * | 7/1998 | Vivekanandan | G01N 22/04 324/640 |
| 6,137,437 A | 10/2000 | Lin et al. | |
| 7,095,359 B2 | 8/2006 | Matsuoka et al. | |
| 8,581,772 B2 | 11/2013 | Long et al. | |
| 2010/0171651 A1 * | 7/2010 | Scheiber | G01S 7/2813 342/179 |
| 2013/0099960 A1 | 4/2013 | Broman et al. | |
| 2014/0062764 A1 | 3/2014 | Reis et al. | |
| 2014/0159936 A1 | 6/2014 | Medlin et al. | |
| 2014/0159937 A1 | 6/2014 | Beadle et al. | |
| 2014/0159938 A1 | 6/2014 | Shipley et al. | |
| 2014/0313072 A1 | 10/2014 | Soofi et al. | |

* cited by examiner

ICE ANALYSIS BASED ON ACTIVE AND PASSIVE RADAR IMAGES

CROSS REFERENCE TO RELATED APPLICATIONS

This application claims priority to and the benefit of U.S. Provisional Application No. 62/074,114 filed on Nov. 3, 2014, the entire contents of which are hereby incorporated herein by reference.

TECHNICAL FIELD

Example embodiments generally relate to ice analysis and, in particular, relate to ice analysis based on radar and radiometer images.

BACKGROUND

Current methods for determining the characteristics of sea ice include using active and passive radio-frequency (RF) sensors to correlate measured RF properties with the physical characteristics of the sea ice. The RF characteristics measured may be normalized radar cross section ($\sigma_0$) and brightness temperature ($T_B$), or reflectivity (r) and emissivity (e). In some ice characterizations both active and passive RF systems are used. However these ice characterizations have been at the algorithm level. In an example, ice concentration data may be retrieved from either single-channel or multi-frequency passive RF systems, and ice concentrations from the same area, but not necessarily acquired simultaneously, may be retrieved from single-frequency active RF systems. The results may be inter-compared for selected areas. Although RMS differences between the active and passive RF algorithms may generally be on the order of 10%, within the range of variability for each sensor algorithm, the lack of time coincidence significantly decreases the agreement for small areas, and increases the error in any one sensor measurement. Some of the disagreement and error may be due to changes in surface conditions between the time of acquiring the RF data and the passive RF data, such as during the summer melt. In addition, because the example synthetic aperture radar (SAR) and passive sensors used for the inter-comparison are single-frequency, inter-comparison of ice type determination may not be possible.

BRIEF SUMMARY OF SOME EXAMPLES

Accordingly, some example embodiments may enable the provision of an ice analyzer including processing circuitry configured to receive a radiometer image including a geographic area including ice, receive a radar image including at least a portion of the geographic area, perform ice/water discrimination of the radiometer image and the radar image, generate a passive ice/water mask and an active ice/water mask based on the ice/water discrimination, merge the passive ice/water mask and the active ice/water mask into a typing mask, and type the ice based on the typing mask.

In another example embodiment, an ice analyzer method is provided including receiving a radiometer image including a geographic area including ice, receiving a radar image including at least a portion of the geographic area, performing ice/water discrimination of the radiometer image and the radar image, generating a passive ice/water mask and an active ice/water mask based on the ice/water discrimination, merging the passive ice/water mask and the active ice/water mask into a typing mask, and typing the ice based on the typing mask.

BRIEF DESCRIPTION OF THE SEVERAL VIEWS OF THE DRAWING(S)

Having thus described the an ice analyzer in general terms, reference will now be made to the accompanying drawings, which are not necessarily drawn to scale, and wherein:

DETAILED DESCRIPTION

Figure 1:
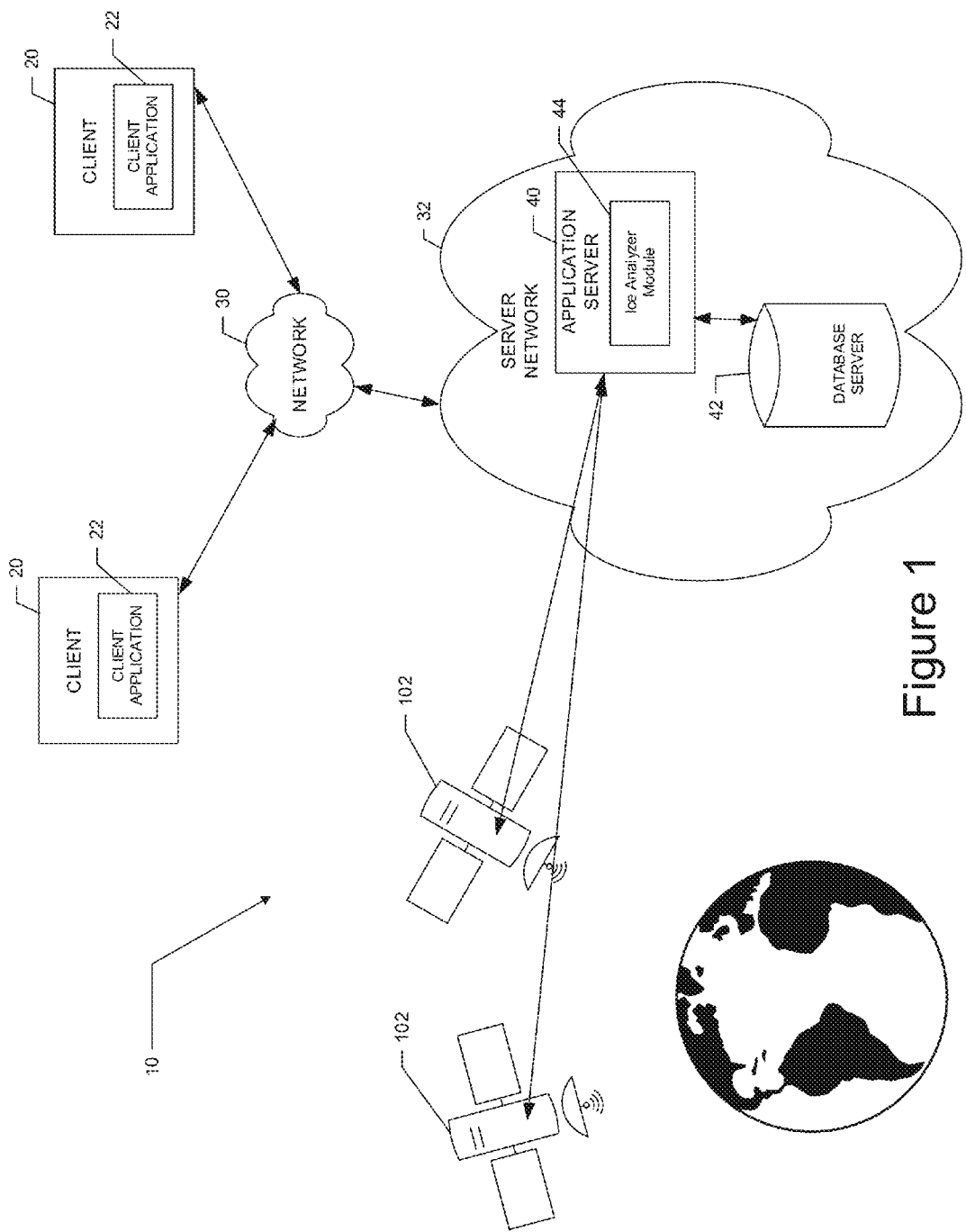
FIG. 1 illustrates a system for ice analysis according to an example embodiment.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. As used herein, operable coupling should be understood to relate to direct or indirect connection that, in either case, enables functional interconnection of components that are operably coupled to each other.

As used in herein, the terms "component," "module," and the like are intended to include a computer-related entity, such as but not limited to hardware, firmware, or a combination of hardware and software. For example, a component or module may be, but is not limited to being, a process running on a processor, a processor, an object, an executable, a thread of execution, and/or a computer. By way of example, both an application running on a computing device and/or the computing device can be a component or module. One or more components or modules can reside within a process and/or thread of execution and a component/module may be localized on one computer and/or distributed between two or more computers. In addition, these components can execute from various computer readable media having various data structures stored thereon. The components may communicate by way of local and/or remote processes such as in accordance with a signal having one or more data packets, such as data from one component/module interacting with another component/module in a local system, distributed system, and/or across a network such as the Internet with other systems by way of the signal. Each respective component/module may perform one or more functions that will be described in greater detail herein. However, it should be appreciated that although this example is described in terms of separate modules corresponding to various functions performed, some examples may not necessarily utilize modular architectures for employment of the respective different functions. Thus, for example, code may be shared between different modules, or the processing circuitry itself may be configured to perform all of the functions described as being associated with the components/modules described herein. Furthermore, in the context of this disclosure, the term "module" should not be understood as a nonce word to identify any generic means for performing functionalities of the respective modules. Instead, the term "module" should be understood to be a modular component that is specifically configured in, or can be operably coupled to, the processing circuitry to modify the behavior and/or capability of the processing circuitry based on the hardware and/or software that is added to or otherwise operably coupled to the processing circuitry to configure the processing circuitry accordingly.

In some example embodiments, a method of ice analysis is provided including generating an ice/water mask for a radar image, e.g. a passive ice/water mask, and a radiometer image, e.g. an active ice/water mask including a common geographic area. The ice masks may be generated based on an ice/water discrimination that uses coefficient of variation on the radar image and polarization ratios on the radiometer image. Once the ice masks are generated the passive ice/water mask may be merged with the active ice/water mask into a typing mask. The ice analyzer may type the ice based on the typing mask.

In some embodiments, the radiometer image and the radar image may be registered based on geographic location. Registering the radiometer image with the radar image may be beneficial to reduce errors due to radar image misalignment.

In an example embodiment, the ice analysis method may apply a land mask to exclude pixels in the radiometer image from further analysis. Similarly, pixels which are at or near the ice edge may also be excluded from further analysis. The ice analysis for land and ice edge may be based on the radar image, which in some examples has a significantly higher pixel to land area ratio.

In an example embodiment, adaptive coefficient of variation (COV) thresholding may be applied to the active ice/water mask. The adaptive COV thresholding may be beneficial for reducing meteorological effects and effects of thin ice. Sea spikes may also be reduced by cross referencing the active ice/water mask to passive polarization ratios away from the ice edge, a spatial density check, or the like.

In some example embodiments, the radiometer image and the radar image may be captured by RF systems operating in C band. Utilization of C band may mitigate the effects of seasonal surface melt and snow effects, relative to X band or higher frequencies.

In an example embodiment, the radar images may be captured by a radar operating with dual polarization, such as horizontal transmit-horizontal receive (HH) and horizontal transmit-vertical receive (HV). The radiometer images may be captured by a radiometer operating with dual polarization, measuring horizontally-polarized (H) and vertically-polarized (V) self-emissions from the surface. The ice analyzer may determine a polarization ratio for use in the ice/water discrimination.

In some example embodiments, the radiometer image and the radar image may be captured contemporaneously or near contemporaneously. The contemporaneous capture of the radiometer image and radar image may be beneficial for condition normalization between the radiometer image and the radar image. In an example embodiment, contemporaneous may include capture of the radiometer image within 1 hour, 6 hours, 12 hours, or the like, of the radar image.

Example System

An example embodiment of the invention will now be described in reference to FIG. 1, which illustrates an example system in which an embodiment of the present invention may be employed. As shown in FIG. 1, a system 10 according to an example embodiment may include one or more client devices (e.g., clients 20). Notably, although FIG. 1 illustrates two clients 20, it should be appreciated that a single client or many more clients 20 may be included in some embodiments and thus, the two clients 20 of FIG. 1 are simply used to illustrate a potential for a multiplicity of clients 20 and the number of clients 20 is in no way limiting to other example embodiments. In this regard, example embodiments are scalable to inclusion of any number of clients 20 being tied into the system 10. Furthermore, in some cases, some embodiments may be practiced on a single client without any connection to the system 10.

The example described herein will be related to an asset comprising a computer or analysis terminal to illustrate one example embodiment. However, it should be appreciated that example embodiments may also apply to any asset including, for example, any programmable device that is capable of receiving and analyzing radar images as described herein.

Each one of the clients 20 may include or otherwise be embodied as computing device (e.g., a computer, a network access terminal, a personal digital assistant (PDA), cellular phone, smart phone, or the like) capable of communication with a network 30. As such, for example, each one of the clients 20 may include (or otherwise have access to) memory for storing instructions or applications for the performance of various functions and a corresponding processor for executing stored instructions or applications. Each one of the clients 20 may also include software and/or corresponding hardware for enabling the performance of the respective functions of the clients 20 as described below. In an example embodiment, one or more of the clients 20 may include a client application 22 configured to operate in accordance with an example embodiment of the present invention. In this regard, for example, the client application 22 may include software for enabling a respective one of the clients 20 to communicate with the network 30 for requesting and/or receiving information and/or services via the network 30. Moreover, in some embodiments, the information or services that are requested via the network may be provided in software as a service (SAS) environment. The information or services receivable at the client applications 22 may include deliverable components (e.g., downloadable software to configure the clients 20, or information for consumption/processing at the clients 20). As such, for example, the client application 22 may include corresponding executable instructions for configuring the client 20 to provide corresponding functionalities for ice analysis, as described in greater detail below.

The network 30 may be a data network, such as a local area network (LAN), a metropolitan area network (MAN), a wide area network (WAN) (e.g., the Internet), and/or the like, which may couple the clients 20 to devices such as processing elements (e.g., personal computers, server computers or the like) and/or databases. Communication between the network 30, the clients 20 and the devices or databases (e.g., servers) to which the clients 20 are coupled may be accomplished by either wireline or wireless communication mechanisms and corresponding communication protocols.

In an example embodiment, devices to which the clients 20 may be coupled via the network 30 may include one or more application servers (e.g., application servers 40), and/or a database servers 42, which together may form respective elements of a server network 32. Notably, although FIG. 1 illustrates a server network 32, it should be appreciated that a multiple server network 32 may be included in some embodiments and thus, the single server network of FIG. 1 is simply used to illustrative and is in no way limiting to other example embodiments. In this regard, example embodiments are scalable to inclusion of any number of server networks being tied into the system 10. Similarly, a network server may have one or a plurality of Application servers 40 and/or database servers 42. Although the application server 40 and the database server 42 are each referred to as "servers," this does not necessarily imply that they are embodied on separate servers or devices. As such, for example, a single server or device may include both entities and the database server 42 could merely be represented by a database or group of databases physically located on the same server or device as the application server 40. The application server 40 and the database server 42 may each include hardware and/or software for configuring the application server 40 and the database server 42, respectively, to perform various functions. As such, for example, the application server 40 may include processing logic and memory enabling the application server 40 to access and/or execute stored computer readable instructions for performing various functions. In an example embodiment, one function that may be provided by the application server 40 may be the provision of access to information and/or services related to operation of the terminals or computers with which the clients 20 are associated. For example, the application server 40 may be configured to provide for storage of information descriptive of radar images (e.g., selection radiometer or radar images received from one or more satellites 102, as discussed below). In some cases, these contents may be stored in the database server 42. Alternatively or additionally, the application server 40 may be configured to provide analytical tools for use by the clients 20 in accordance with example embodiments.

In some embodiments, for example, the application server 40 may therefore include an instance of an ice analyzer module 44 comprising stored instructions for handling activities associated with practicing example embodiments as described herein. As such, in some embodiments, the clients 20 may access the ice analyzer module 44 online and utilize the services provided thereby. However, it should be appreciated that in other embodiments, the ice analyzer module 44 may be provided from the application server 40 (e.g., via download over the network 30) to one or more of the clients 20 to enable recipient clients to instantiate an instance of the ice analyzer module 44 for local operation. As yet another example, the ice analyzer module 44 may be instantiated at one or more of the clients 20 responsive to downloading instructions from a removable or transferable memory device carrying instructions for instantiating the ice analyzer module 44 at the corresponding one or more of the clients 20. In such an example, the network 30 may, for example, be a peer-to-peer (P2P) network where one of the clients 20 includes an instance of the ice analyzer module 44 to enable the corresponding one of the clients 20 to act as a server to other clients 20. In a further example embodiment, the ice analyzer module 44 may be distributed amongst one or more clients 20 and/or the application server 40.

In an example embodiment, the application server 40 may include or have access to memory (e.g., internal memory or the database server 42) for storing instructions or applications for the performance of various functions and a corresponding processor for executing stored instructions or applications. For example, the memory may store an instance of the ice analyzer module 44 configured to operate in accordance with an example embodiment of the present invention. In this regard, for example, the ice analyzer module 44 may include software for enabling the application server 40 to communicate with the network 30 and/or the clients 20 for the provision and/or receipt of information associated with performing activities as described herein. Moreover, in some embodiments, the application server 40 may include or otherwise be in communication with an access terminal (e.g., a computer including a user interface) via which analysts may interact with, configure or otherwise maintain the system 10.

The application server 40 may be in data communication with one or more satellites 102. The data communication may be an RF downlink, such as K band, Ka band, or any other suitable RF communication band. The satellites 102 may be configured to capture radar images of geographic areas, such as the Arctic Circle. In an example embodiment, the RF images may include radiometer images and/or radar images. In an example embodiment, the radar images may be captured in dual polarization, for example horizontal-transmit-vertical receive (HV) and horizontal-transmit-horizontal receive (HH). The radiometer images may be captured in dual polarization as horizontally-polarized (H) and vertically-polarized (V). The radar and radiometer images may be received by the application server 40 and stored in the server database 42.

Example Apparatus

Figure 2:
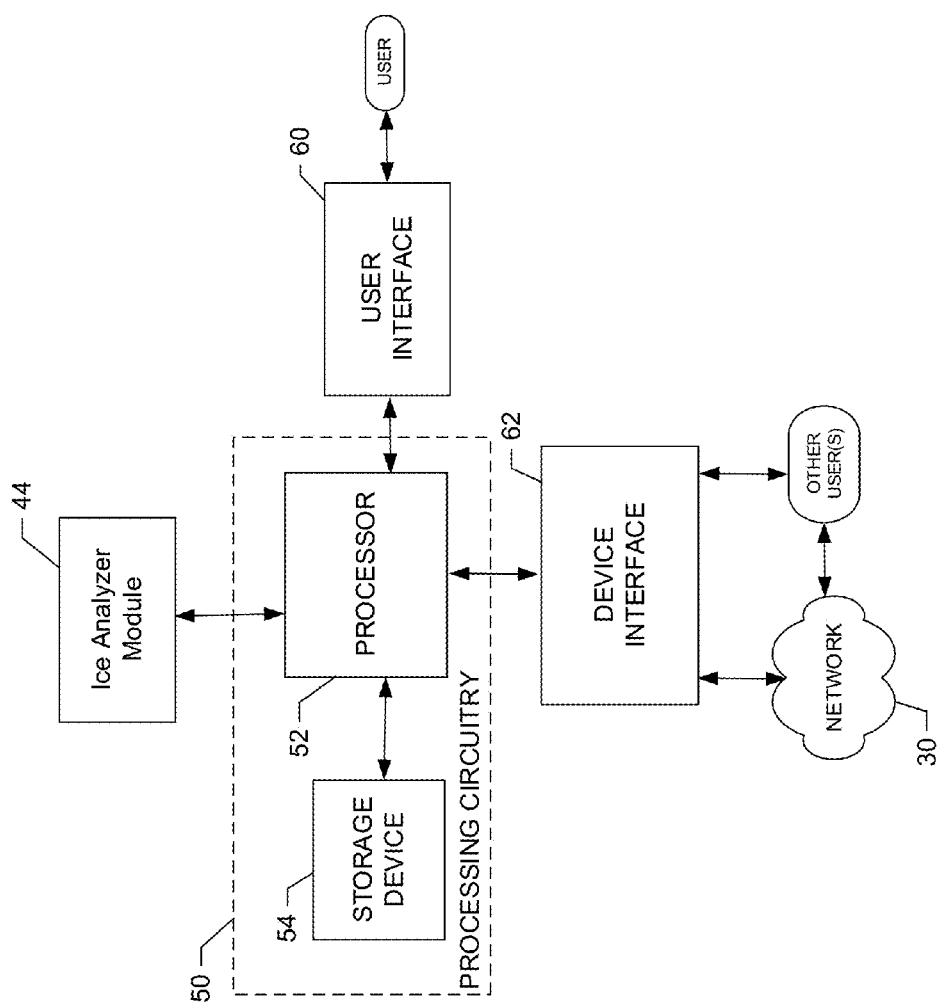
FIG. 2 illustrates an example apparatus for ice analysis according to an example embodiment.

An example embodiment of the invention will now be described with reference to FIG. 2. FIG. 2 shows certain elements of an apparatus for ice analysis based on radar and radiometer images, e.g. an ice analyzer according to an example embodiment. The apparatus of FIG. 2 may be employed, for example, on a client (e.g., any of the clients 20 of FIG. 1) or a variety of other devices (such as, for example, a network device, server, proxy, or the like (e.g., the application server 40 of FIG. 1)). Alternatively, embodiments may be employed on a combination of devices. Accordingly, some embodiments of the present invention may be embodied wholly at a single device (e.g., the application server 40 or one or more clients 20) or by devices in a client/server relationship (e.g., the application server 40 and one or more clients 20). Furthermore, it should be noted that the devices or elements described below may not be mandatory and thus some may be omitted in certain embodiments.

Referring now to FIG. 2, an apparatus configured for ice analysis based on radar and radiometer images is provided. The apparatus may be an embodiment of the ice analyzer module 44 or a device hosting the ice analyzer module 44. As such, configuration of the apparatus as described herein may transform the apparatus into the ice analyzer module 44. In an example embodiment, the apparatus may include or otherwise be in communication with processing circuitry 50 that is configured to perform data processing, application execution and other processing and management services according to an example embodiment of the present invention. In one embodiment, the processing circuitry 50 may include a storage device 54 and a processor 52 that may be in communication with or otherwise control a user interface 60 and a device interface 62. As such, the processing circuitry 50 may be embodied as a circuit chip (e.g., an integrated circuit chip) configured (e.g., with hardware, software or a combination of hardware and software) to perform operations described herein. However, in some embodiments, the processing circuitry 50 may be embodied as a portion of a server, computer, laptop, workstation or even one of various mobile computing devices. In situations where the processing circuitry 50 is embodied as a server or at a remotely located computing device, the user interface 60 may be disposed at another device (e.g., at a computer terminal or client device such as one of the clients 20) that may be in communication with the processing circuitry 50 via the device interface 62 and/or a network (e.g., network 30).

The user interface 60 may be in communication with the processing circuitry 50 to receive an indication of a user input at the user interface 60 and/or to provide an audible, visual, mechanical or other output to the user. As such, the user interface 60 may include, for example, a keyboard, a mouse, a joystick, a display, a touch screen, a microphone, a speaker, a cell phone, or other input/output mechanisms. In embodiments where the apparatus is embodied at a server or other network entity, the user interface 60 may be limited or even eliminated in some cases. Alternatively, as indicated above, the user interface 60 may be remotely located.

The device interface 62 may include one or more interface mechanisms for enabling communication with other devices and/or networks. In some cases, the device interface 62 may be any means such as a device or circuitry embodied in either hardware, software, or a combination of hardware and software that is configured to receive and/or transmit data from/to a network and/or any other device or module in communication with the processing circuitry 50. In this regard, the device interface 62 may include, for example, an antenna (or multiple antennas) and supporting hardware and/or software for enabling communications with a wireless communication network and/or a communication modem or other hardware/software for supporting communication via cable, digital subscriber line (DSL), universal serial bus (USB), Ethernet or other methods. In situations where the device interface 62 communicates with a network, the network may be any of various examples of wireless or wired communication networks such as, for example, data networks like a Local Area Network (LAN), a Metropolitan Area Network (MAN), and/or a Wide Area Network (WAN), such as the Internet.

In an example embodiment, the storage device 54 may include one or more non-transitory storage or memory devices such as, for example, volatile and/or non-volatile memory that may be either fixed or removable. The storage device 54 may be configured to store information, data, applications, instructions or the like for enabling the apparatus to carry out various functions in accordance with example embodiments of the present invention. For example, the storage device 54 could be configured to buffer input data for processing by the processor 52. Additionally or alternatively, the storage device 54 could be configured to store instructions for execution by the processor 52. As yet another alternative, the storage device 54 may include one of a plurality of databases (e.g., database server 42) that may store a variety of files, contents or data sets. Among the contents of the storage device 54, applications (e.g., client application 22 or service application 42) may be stored for execution by the processor 52 in order to carry out the functionality associated with each respective application.

The processor 52 may be embodied in a number of different ways. For example, the processor 52 may be embodied as various processing means such as a microprocessor or other processing element, a coprocessor, a controller or various other computing or processing devices including integrated circuits such as, for example, an ASIC (application specific integrated circuit), an FPGA (field programmable gate array), a hardware accelerator, or the like. In an example embodiment, the processor 52 may be configured to execute instructions stored in the storage device 54 or otherwise accessible to the processor 52. As such, whether configured by hardware or software methods, or by a combination thereof, the processor 52 may represent an entity (e.g., physically embodied in circuitry) capable of performing operations according to embodiments of the present invention while configured accordingly. Thus, for example, when the processor 52 is embodied as an ASIC, FPGA or the like, the processor 52 may be specifically configured hardware for conducting the operations described herein. Alternatively, as another example, when the processor 52 is embodied as an executor of software instructions, the instructions may specifically configure the processor 52 to perform the operations described herein.

In an example embodiment, the processor 52 (or the processing circuitry 50) may be embodied as, include or otherwise control the ice analyzer module 44, which may be any means, such as, a device or circuitry operating in accordance with software or otherwise embodied in hardware or a combination of hardware and software (e.g., processor 52 operating under software control, the processor 52 embodied as an ASIC or FPGA specifically configured to perform the operations described herein, or a combination thereof) thereby configuring the device or circuitry to perform the corresponding functions of the ice analyzer module 44 as described below.

The ice analyzer module 44 may include tools to facilitate ice analysis via the network 30. In an example embodiment, the ice analyzer module 44 may be configured for receiving a radiometer image including a geographic area including ice, receiving a radar image including at least a portion of the geographic area, performing ice/water discrimination of the radiometer image and the radar image, generating a passive ice/water mask and an active ice/water mask based on the ice/water discrimination, merging the passive ice/water mask and the active ice/water mask into a typing mask, and typing the ice based on the typing mask.

Example Ice Analysis Based on Radiometer and Radar Images

RF images may be captured by one or more satellites 102. The satellites 102 may include RF systems configured to capture radiometer images, radar images, or both. The satellites 102 may operate an RF system, such as a radar, in C band, e.g. 4-8 GHz to capture the radiometer and/or radar images. In some example embodiments, the satellites 102 may include RF systems, such as radars, operating with dual polarization, e.g. horizontal transmit-horizontal receive (HH) and horizontal transmit-vertical receive (HV) for capturing the radar images and horizontally-polarized (H) and vertically-polarized (V) for the radiometer images. The radar images may be transmitted to terrestrial receiver associated with data storage, such as the database server 42. The radiometer and radar images may be time stamped or otherwise annotated to capture time cross comparisons, such as storing contemporaneously captured radar images in a common memory location.

In an example embodiment, the radar of the satellites 102 may be a passive RF system. The passive RF system may sense self-emissions from a surface of earth, and different materials, being composed of different elements, produce different emission levels at different RF lengths. As ice thickens from frazil through to multi-year ice, the salinity of the ice drops from that of seawater to nearly that of fresh water, and the ice structure changes from uncongealed globules to relatively large, vertically oriented platelets. Brightness temperature of the resultant radiometer image may increase rapidly with increasing thickness to 15 cm thick young ice with a much slower rise thereafter, regardless of frequency or polarization of the radar. Passive RF systems may detect thin ice types from space. In some examples, the aerial extent of the thinner ice may cover most of a large satellite passive pixel for detection.

In an example embodiment, the radar of the satellites 102 may be an active RF system. In active RF systems, normalized radar cross sections of ice may be a function of the dielectric constant and roughness of the ice. Volume scattering may be driven by the dielectric constant of the ice and surface scattering may be driven by the roughness of the ice surface.

"New ice," as used herein, is recently formed ice which includes frazil ice, grease ice, slush, and shuga composed of ice crystals which are only weakly frozen together (if at all) and have a definite form only while they are afloat. New ice may be highly saline, but because new ice begins as uncongealed globules suspended just below the water surface. The new ice may dampen the short wind-generated and short gravity waves that are in resonance with radar backscattering. Like surface slicks, the dampening of the short-wind generated and short gravity waves may produce a darkened surface in the radar image. As the ice thickens, the ice may roughen, producing higher cross sections.

"Young ice," as used herein, is ice in the transition stage between nilas and first-year ice, about 10-30 cm in thickness. At the young ice stage, ice may form at the bottom due to platelet growth, but may also grow on the upper surface as a result of super-chilled vapor in the air above, and draw the salt upward from the subsurface ice/water volume. The salt and water may grow into intersecting platelet structures called frost flowers. The frost flowers may produce an artificially rough surface, with elevated cross-sections proportional to the density of extruded platelets on the ice surface. In some examples, frost flowers may appear, grow, and disappear in the course of a few hours. Ice, with frost flowers, in the thickness range of 2-50 cm may have cross sections that vary on the order of 20 dB above and below the cross section of nearby open water.

"First-year ice," as used herein, is ice of not more than one winter's growth, developing from young ice; 30 cm or greater in thickness. "Multi year ice" as used herein is ice which has survived at least two summer's melt. For first-year and multi-year ice, most of the brine between the water crystals may be far enough below the surface that there is little to be drawn out onto it, and frost flower formation stops. For first-year and multi-year ice, surface roughness may be the result of rafting and ridging, and, later in the season, the formation and draining of meltponds. In an instance in which the ice thickens and becomes less saline, the loss factor of the dielectric constant may decrease by about a factor of four, and the penetration depth may increase by about the same factor of four. The result of these changes is lower cross sections for first-year ice than young ice, and higher cross sections in multi-year ice, as the scattering transitions from surface to volume scatter.

Penetration depth of the radar, e.g. the rough height of the volume of ice sensed by the radar, may be, all other factors held constant, a function of frequency, with longer wavelengths penetrating further into the ice. This may affects both active and passive RF systems, with high frequencies, such as 15 GHz and above, becoming increasingly sensitive to the accumulation of meltwater on the surface of the ice during the summer. Lower frequencies, such as below about 8 GHz, emissivity, for either polarization, may have insignificant changes in sensitivity across the season until late in the melt season. Late in the melt season, the lower frequency may have some change in sensitivity for first-year and thinner ice. Beneficially, the lower frequency radiometers have more uniform emissivity and are less sensitive to seasonal changes in surface conditions. Utilizing both active and passive RF systems at C-band may reduce the seasonal variability of cross section and brightness temperature ranges chosen for ice typing, and may be more robust from Arctic sea to Arctic sea. C-band dual-polarization imagery from RADARSAT-2 and the horizontal polarization and vertical polarization 6 GHz channels of AMSR-E and AMSR-2 were selected for the example described below.

The ice analyzer module 44 may receive a radiometer image and a radar image from a data storage, such as server database 42 or storage device 54. The radar image and the radiometer image may be captured by RF systems of the same or different satellites 102. The radiometer image and radar image may include a geographic area in which a portion of the geographic area is in each radar image.

In an example embodiment, the radiometer image and radar image may be captured contemporaneously or near contemporaneously, e.g. within a predetermined period of time, such as 1 hour, 6 hours, 12 hours, or the like. The difference in capture time may be verified by the ice analyzer module 44 based on time stamps and/or storage location.

In an example embodiment, each pixel in the radiometer and/or radar image may be correlated to a geographic coordinate. For example, each pixel in the radiometer and/or radar image may be geo-located and assigned central latitude and longitude. In an example embodiment, the radiometer image and the radar image pixels may be registered based on the geographic coordinate locations and/or the central latitude and longitude.

Example Application of a Land Mask

A land mask, such as a land mask generated by the Search and Rescue Optimal Planning System (SAROPS), may be applied to the radiometer image and the radar image. Pixels identified, by the land mask that include land may be tagged as land pixels and removed from further ice analysis. Exclusion of the land pixels from the ice analysis may prevent false ice determinations.

In some example embodiments, pixels which include land contamination may be determined to be land fringe. Pixels which are determined to be land fringe may be excluded from further ice analysis in the radiometer image and ice typing, discussed below. Further ice analysis and ice typing for the land fringe may be performed based on corresponding radar image pixels only. The removal of the radiometer image land fringe pixels may remove pixels with land contamination due to the shape of beams used by the passive RF systems, which may be beneficial in the extraction of ice information close to land. The ice information close to land or coasts may be particularly important due the increased human traffic in these areas of polar seas.

Figure 3:
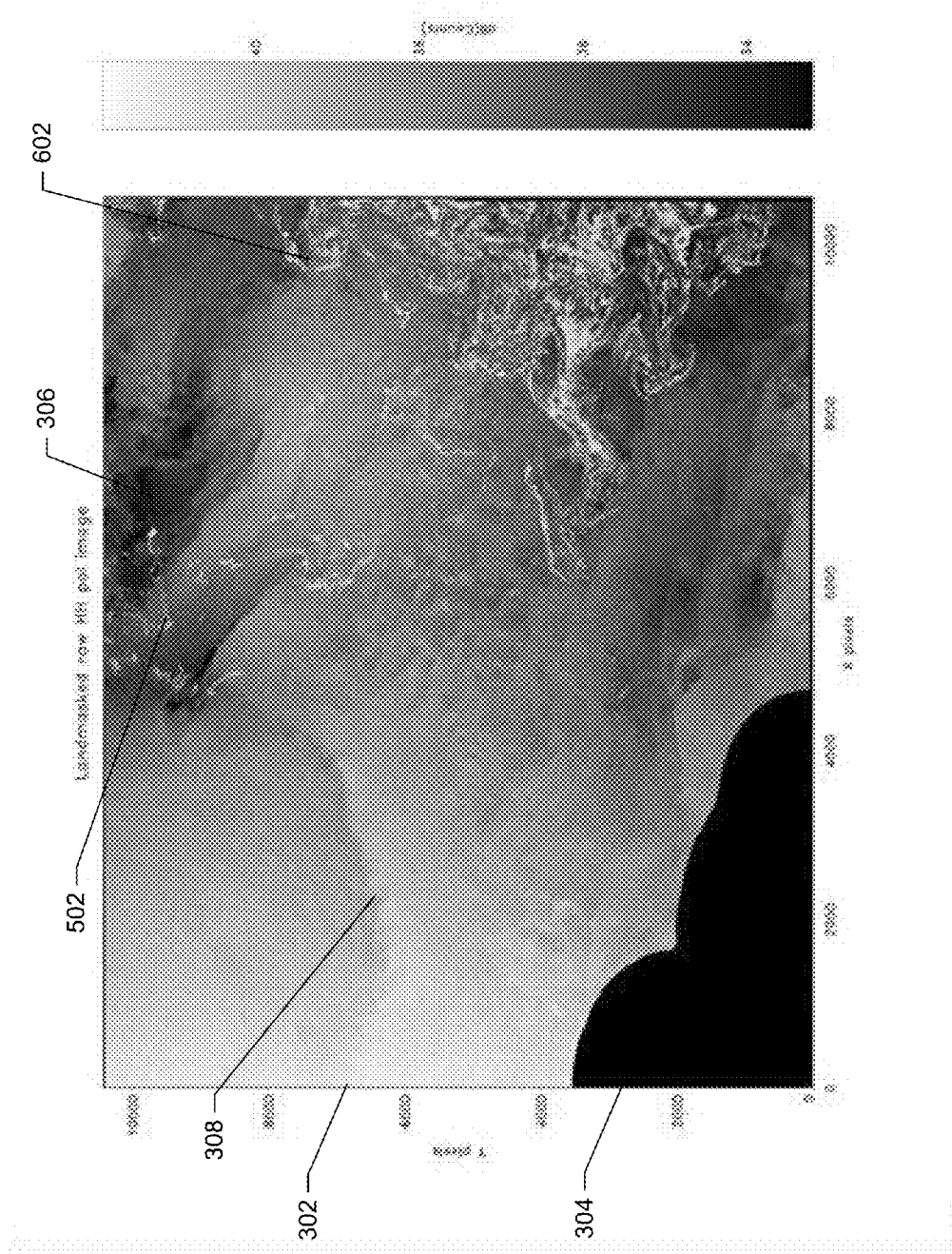
FIGS. 3 and 4 illustrate an example dual polarization radar image according to an example embodiment.

In an example embodiment, land fringe may be determined through a multi-step analysis. First, the land mask may be converted into discontinuous coastlines using a one-active-pixel offset and subtraction technique. The pixels identified as coastline pixels may be tagged as coast pixels. The marked coast pixels may be grouped into blobs with a blob detector. In an example embodiment in which the passive pixels are large (26 km) relative to the active pixels (100 m), only one pixel in the smaller coastline blobs may be selected for testing. A circle, with the selected pixel for testing at its origin and a radius of five passive pixels, may be drawn over the radiometer image. Pixels that were not already found to be in the land mask may be tagged as land fringe. The land pixels and land fringe pixels may be tagged in each radar and radiometer image, e.g. both polarizations, before proceeding to determining the ice/water mask. FIG. 3 illustrates a radar image 302 with a land mask and land fringe mask overlay according to an example embodiment. FIG. 3 includes a horizontal transmit-horizontal receive (HH) polarity of the radar image 302. The radar image 302 of this example is a RADARSAT-2 image of the Beaufort Sea on Sep. 26, 2010. The radar image 302 is in raw data counts, e.g. uncalibrated. The land mask/land fringe mask 304 is applied to the left bottom corner excluding pixels in this area.

Figure 4:
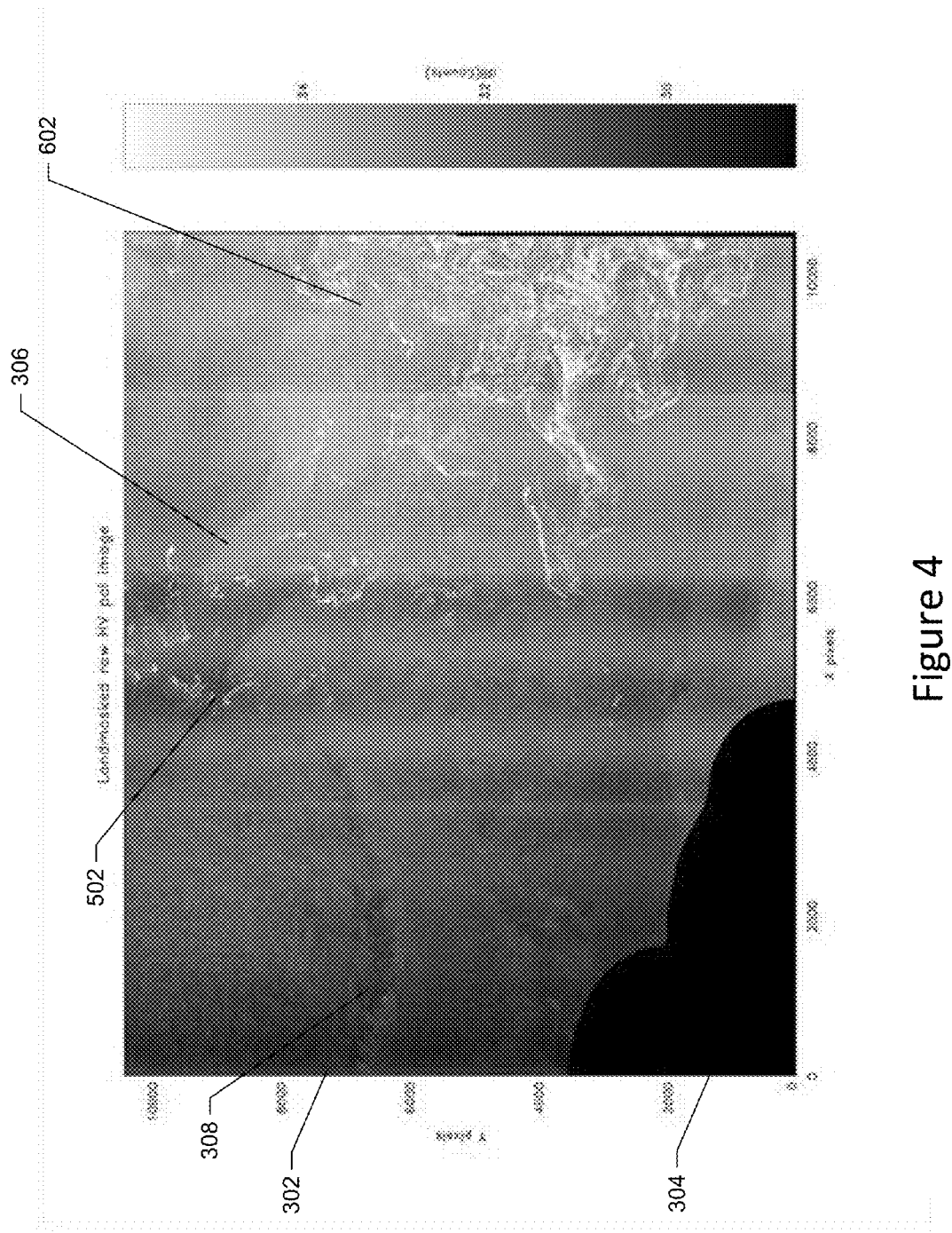

FIG. 4 illustrates a radar image 302 with a land mask and land fringe mask 304 overlay according to an example embodiment. FIG. 4 includes a horizontal transmit-vertical receive (HV) polarity of the radar image 302. The radar image 302 of this example is a RADARSAT-2 image of the Beaufort Sea Sep. 26, 2010. The radar image 302 is in raw data counts, e.g. uncalibrated. The land mask/land fringe mask 304 is applied to the left bottom corner excluding pixels in this area.

Figure 15:
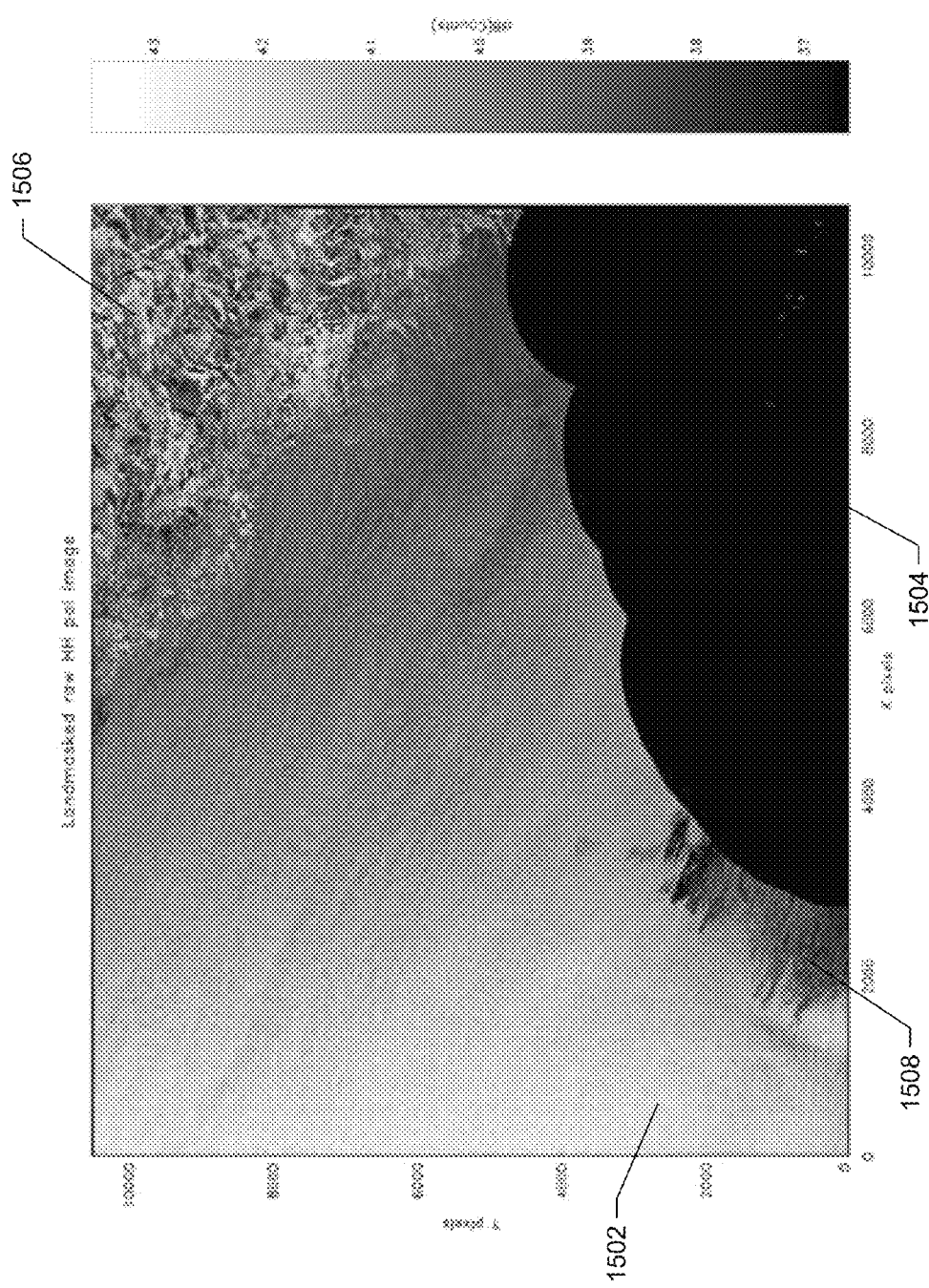
FIGS. 15 and 16 illustrate a second example dual polarization radar image according to an example embodiment.

FIG. 15 illustrates a radar image 1502 with a land mask and land fringe mask 1504 overlay according to an example embodiment. FIG. 15 includes a horizontal transmit-horizontal receive (HH) polarity of the radar image 1502. The radar image 1502 of this example is a RADARSAT-2 image of the Chukchi Sea on Sep. 28, 2010. The land mask/land fringe mask 1504 is applied to the right bottom corner excluding pixels in this area.

Figure 16:
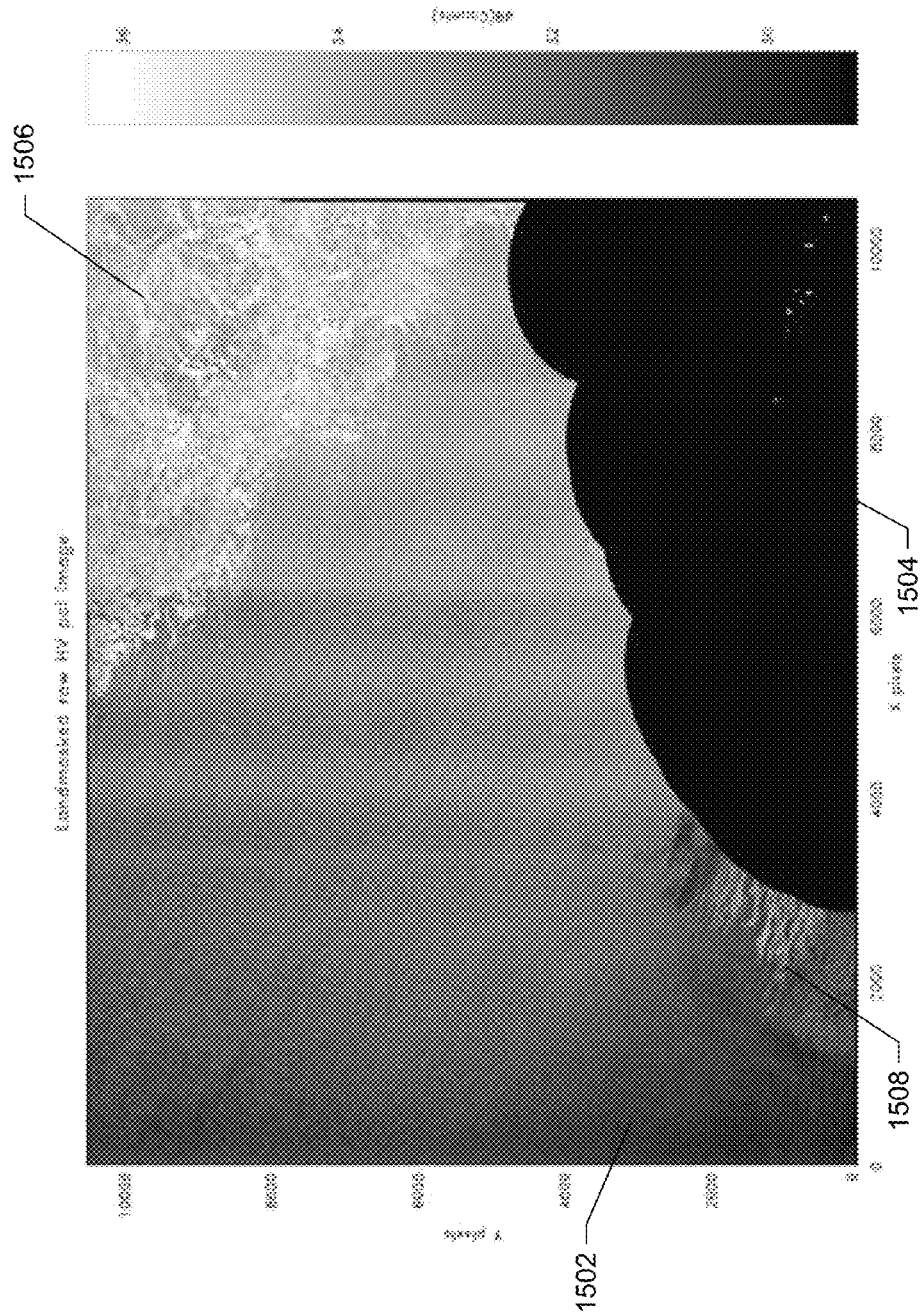

FIG. 16 illustrates a radar image 1502 with a land mask and land fringe mask overlay according to an example embodiment. FIG. 16 includes a horizontal transmit-vertical receive (HV) polarity of the radar image 1502. The radar image 1502 of this example is a RADARSAT-2 image of the Chukchi Sea on Sep. 28, 2010. The land mask/land fringe mask 1504 is applied to the left bottom corner excluding pixels in this area.

Example Ice/Water Mask

An ice/water mask may be generated for the radiometer image, e.g. a passive ice/water mask, based on an ice/water discrimination of the radiometer image. The radiometer image may include the horizontal and vertical polarizations.

Histograms of the pixels remaining after the application of the land mask may be calculated for horizontal polarization and the vertical polarization of the radiometer image. In an instance in which pixels with water brightness temperatures at the RF operating wavelength, e.g. 6 GHz, are present in the region of the radiometer image, the peak of the histogram in the water range may be selected, and the brightness temperature where the histogram falls to one-tenth of the peak value may be selected as the maximum water pixel threshold for each polarization of the radiometer image. The selection of the maximum water pixel threshold may not violate the principle of reserving brightness temperature exclusively for ice typing, because the maximum water pixel threshold selected is at the extreme lowest end of the brightness temperatures (Tb) for 6 GHz, and may be lower than any ice brightness expected. Pixels may be compared to the maximum water pixel threshold value. Pixels in the radiometer image that satisfy the maximum water pixel threshold value, e.g. have a higher Tb value, are tagged as potentially ice, with a final threshold to be determined from the polarization ratios.

A final ice/water decimation threshold may be determined based on polarization ratios. A polarization ratio for a single frequency, $$\frac{T_B^V - T_B^H}{T_B^V + T_B^H}$$

is inversely proportional to ice concentration. Passive polarization ratios may be calculated for each of the collocated passive pixels of the horizontal polarization and the vertical polarization of the radiometer image.

For the potential ice pixels, ice concentrations may be calculated through a simple linear conversion. Since it is not known, a priori, that any one passive pixel when registered with the active image will be 100% ice, the passive polarization ratio ice concentrations may not be used as an absolute truth. The passive polarization ice concentrations may be used to indicate open water, and to identify increased ice concentrations from an ice edge. Since new ice forms at the ice edge, and ice is brighter than water at 6 GHz, the ice edge may be set at the 15% passive polarization ice concentration contour, and a three passive pixel margin is set on either side. Open water seaward of the margin may be treated as ice-free, and provides a discriminator for those active pixels with sea spike signatures that would otherwise be counted as ice, or as false positives. The ice free pixels may be tagged as water.

Figure 5:
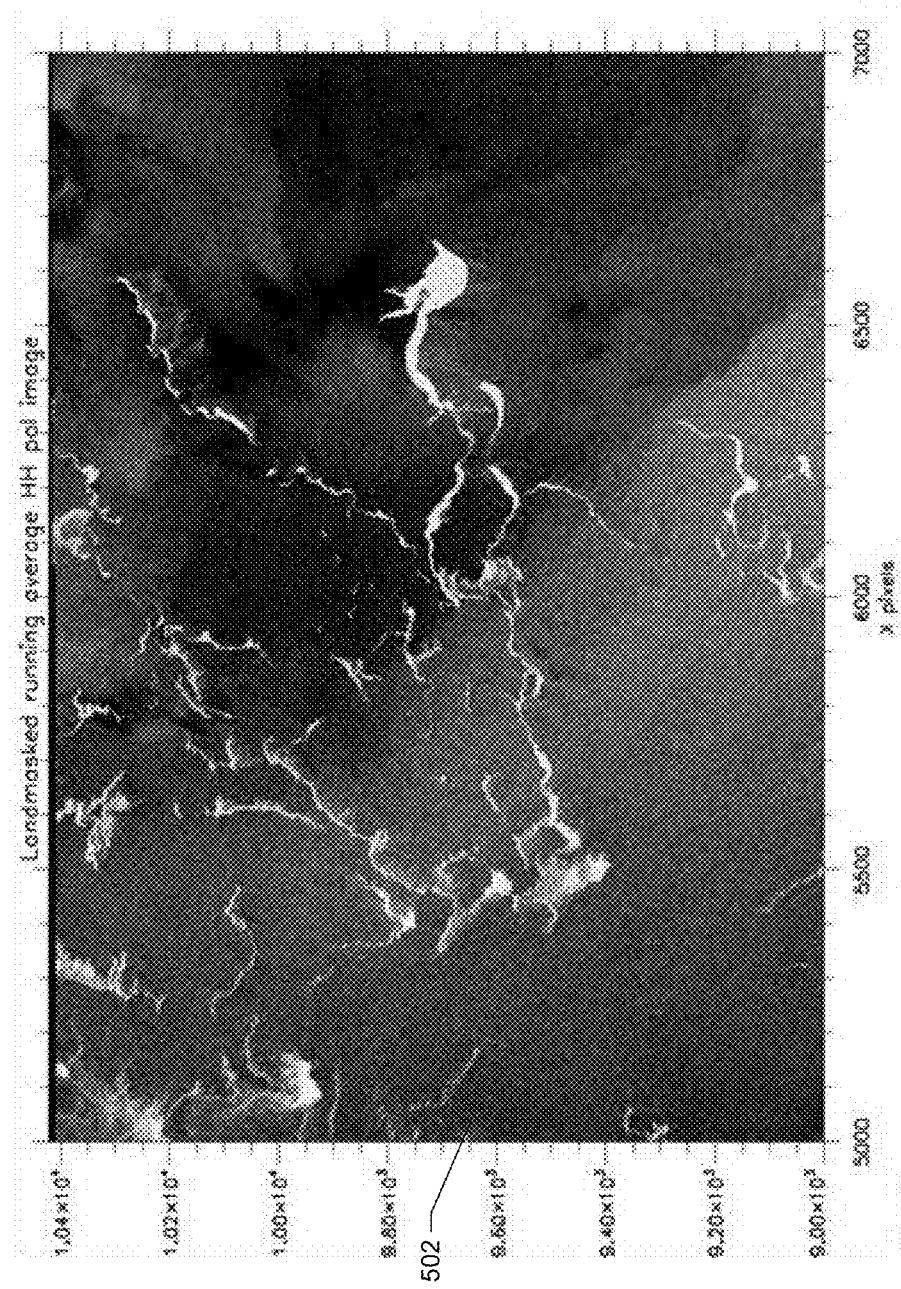
FIGS. 5-8 illustrate magnified areas of the dual polarization radar images according to an example embodiment.
Figure 6:
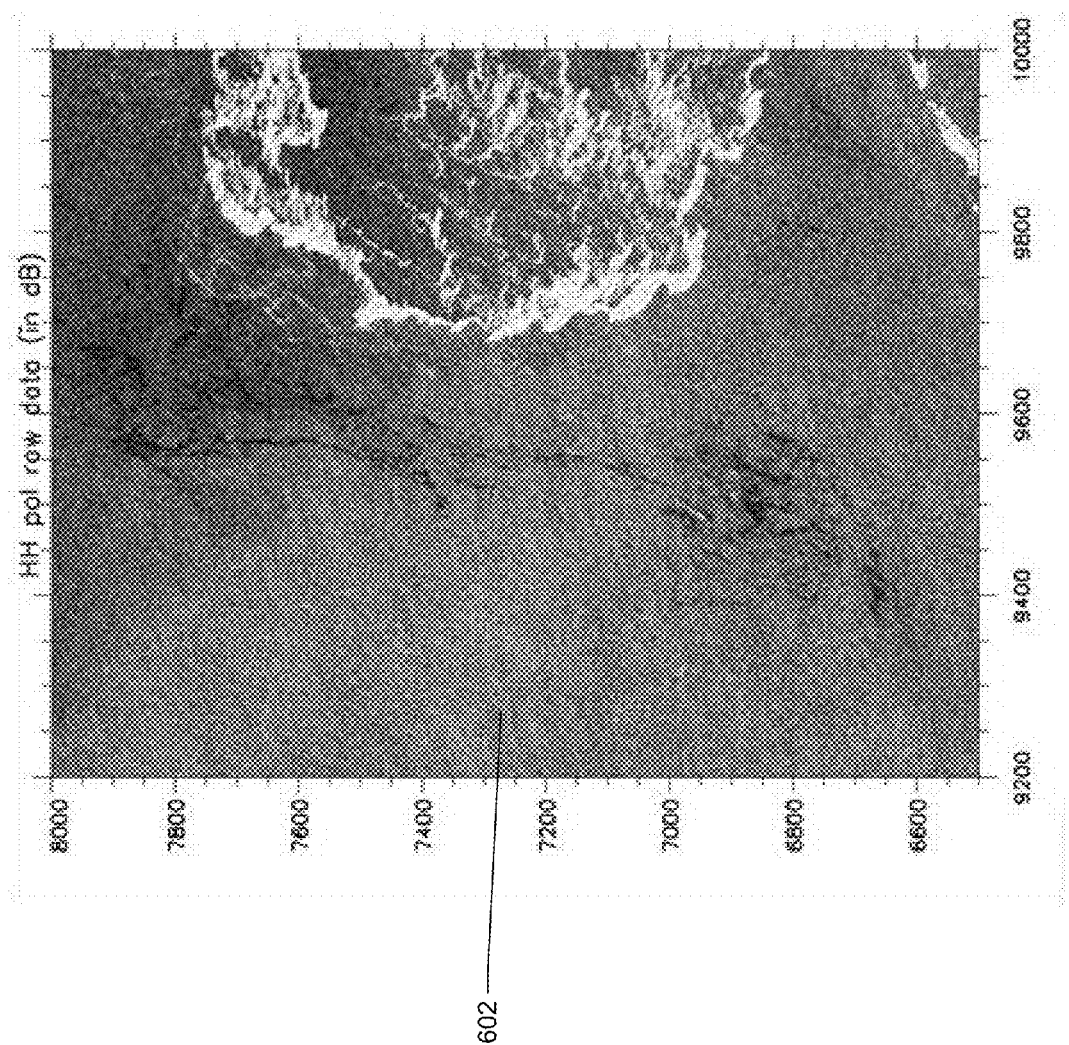
Figure 7:
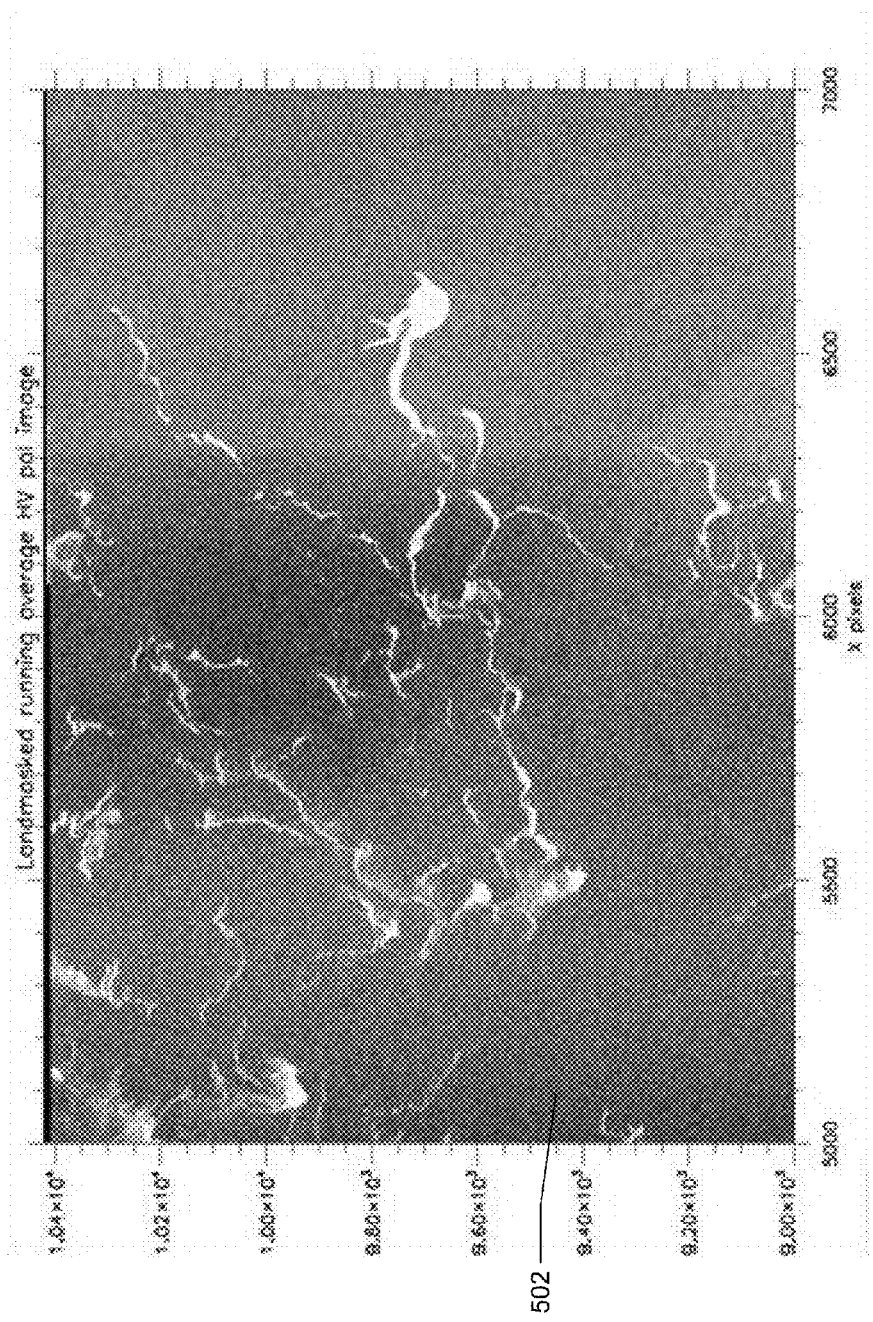
Figure 8:
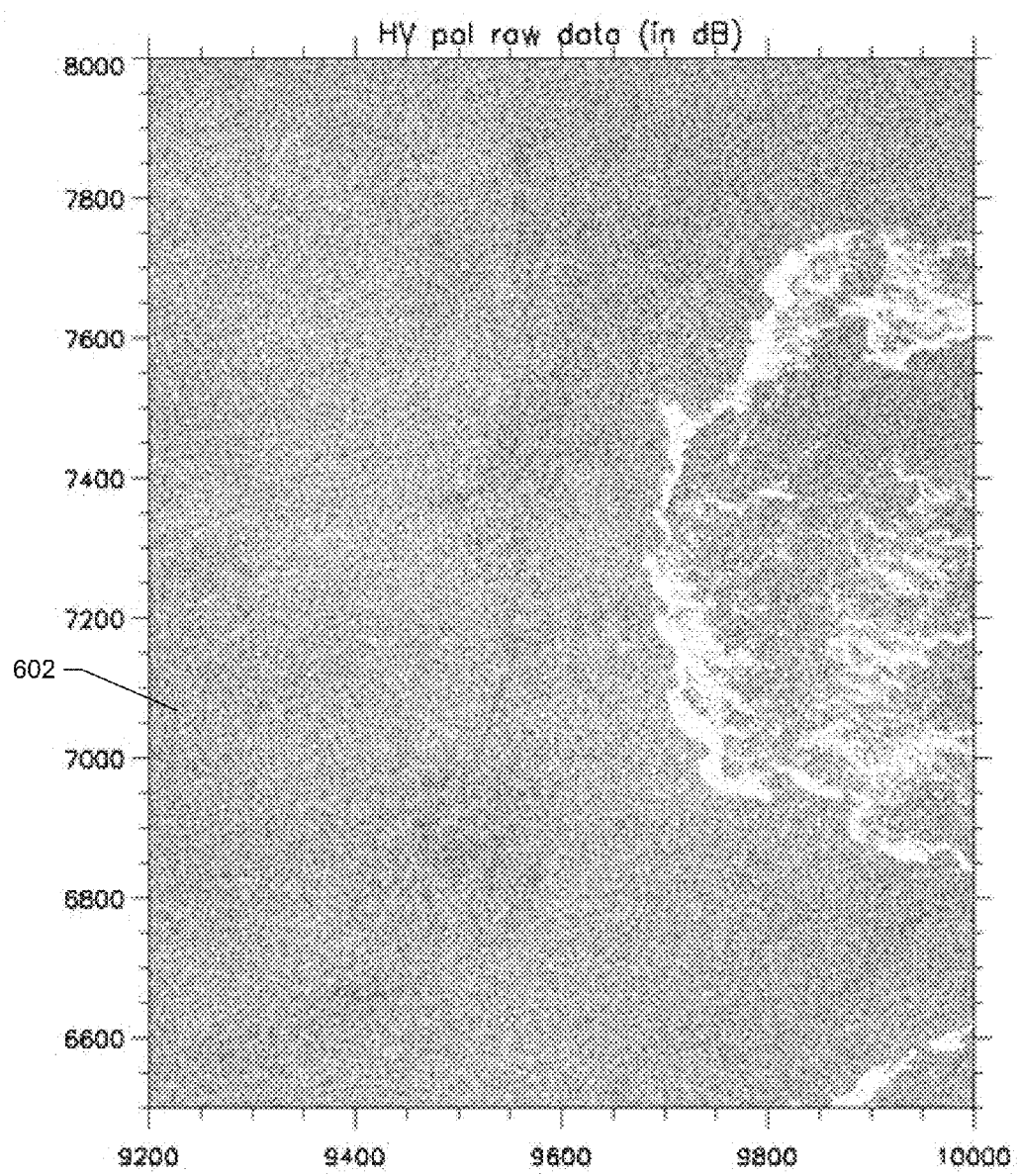

As discussed above, FIGS. 3 and 4 show the HH polarization and the HV polarization of the radar image 302, e.g. dual-polarization RADARSAT-2 image acquired on 26 Sep. 2010 over the Beaufort Sea. The dark area in the lower left has been excluded by the land-mask 304, with the land fringe added to the land mask 304. The ice in this example is highly-degraded late-melt mostly multi-year ice peeled out into belts and strips. A polar low was passing over the area when the image was captured, and the polar low's signature is visible as the circular dark area 306 in the upper right, with lines of down-drafts extending from the center. The downdrafts persist into the center of the image, with signatures as oval dark patches among the multi-year ice. A frontal boundary 308 is present in the upper left of the image. These atmospheric signatures make interpreting this particular radar image for ice and water visually challenging, since the dark line in the upper center of the image (FIG. 5 illustrates a magnified depiction of the HH polarization radar image for the old ice area 502) has the same apparent signature as new ice forming in the center right along the ice edge (FIG. 6 illustrates a magnified depiction of the HH polarization radar image for the new ice area 602). In general, new ice forms in three types of areas at freeze-up, along the coasts in shallow water, where heat can be evacuated from the water column more quickly, in leads between floes, and as depicted in FIGS. 3 and 4, along the ice edge. The atmospheric signatures, while attenuated, are still present in the HV polarization radar image (FIG. 7 illustrates a magnified depiction of the HV polarization radar image for the old ice area 502), while the new ice signature (FIG. 8 illustrates a magnified depiction of the HV polarization radar image for the new ice area 602) is nearly absent.

Figure 9:
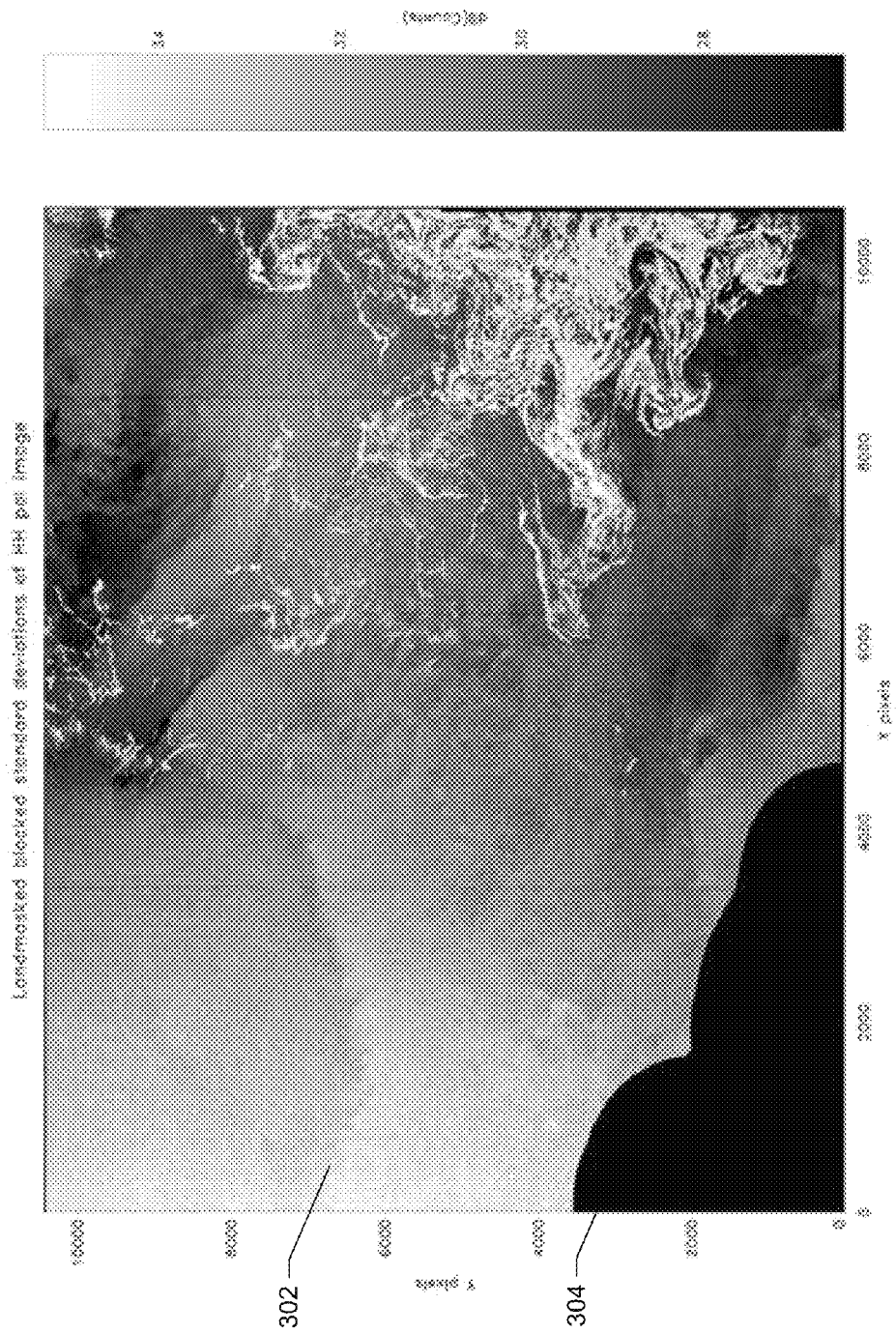
FIG. 9 illustrates a result of a statistical atmosphere signature removal according to an example embodiment.

Several statistical approaches may be implemented to eliminate the atmospheric signatures in the radar image, for example, taking a running averages of ten pixel by ten pixel blocks over the image may diminish the speckle and ameliorate sea spiking or calculating standard deviations over these same running areas, since the atmospheric signatures were broader and less variable than the ice areas. FIG. 9 illustrates the result of the statistical approach to eliminate atmospheric signatures in the radar image 302. As depicted, the atmospheric signatures remain in after either of the running average of calculated standard deviation approaches.

Figure 10:
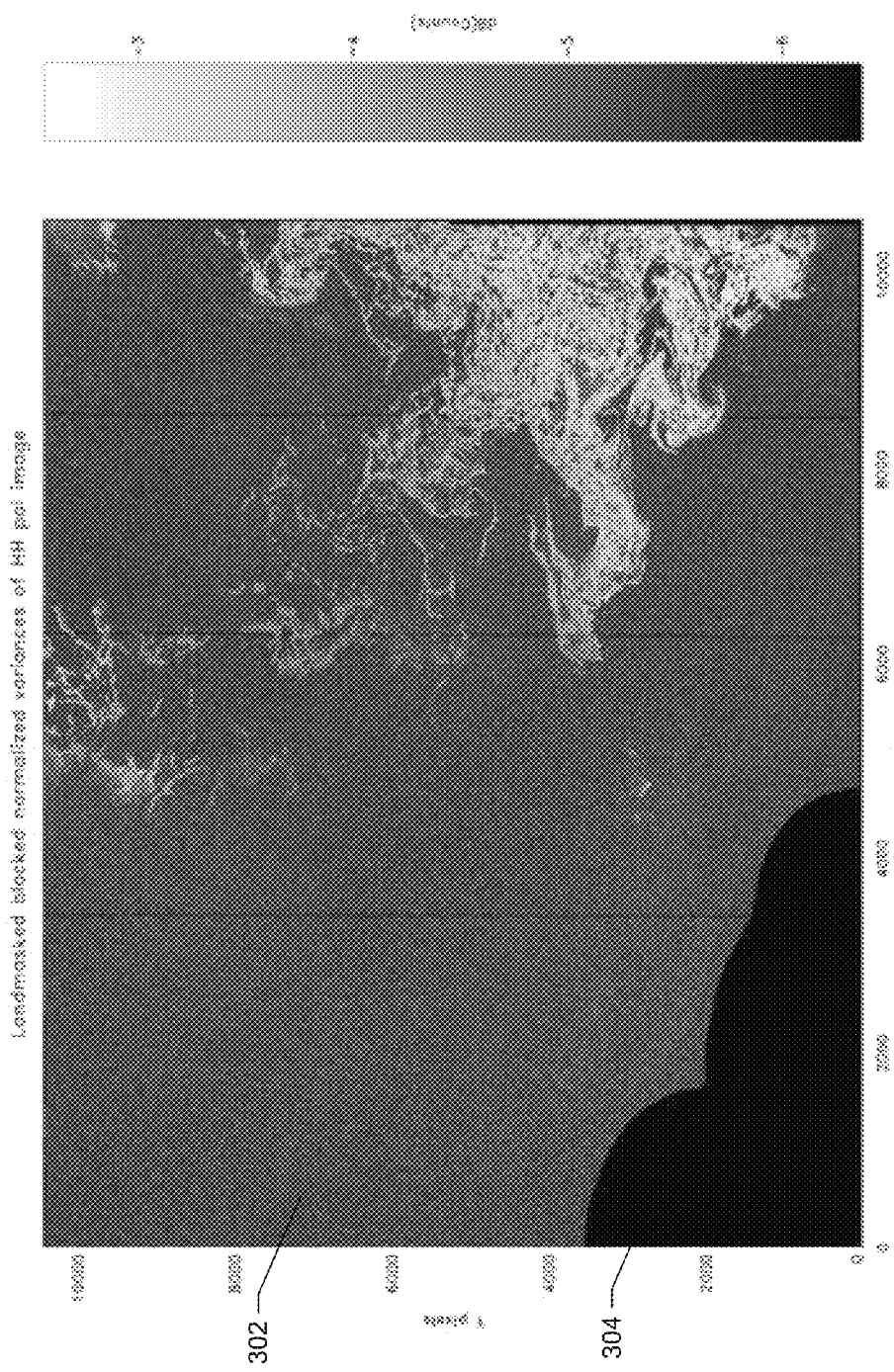
FIG. 10 illustrates a result of a coefficient of variation thresholding according to an example embodiment.
Figure 11:
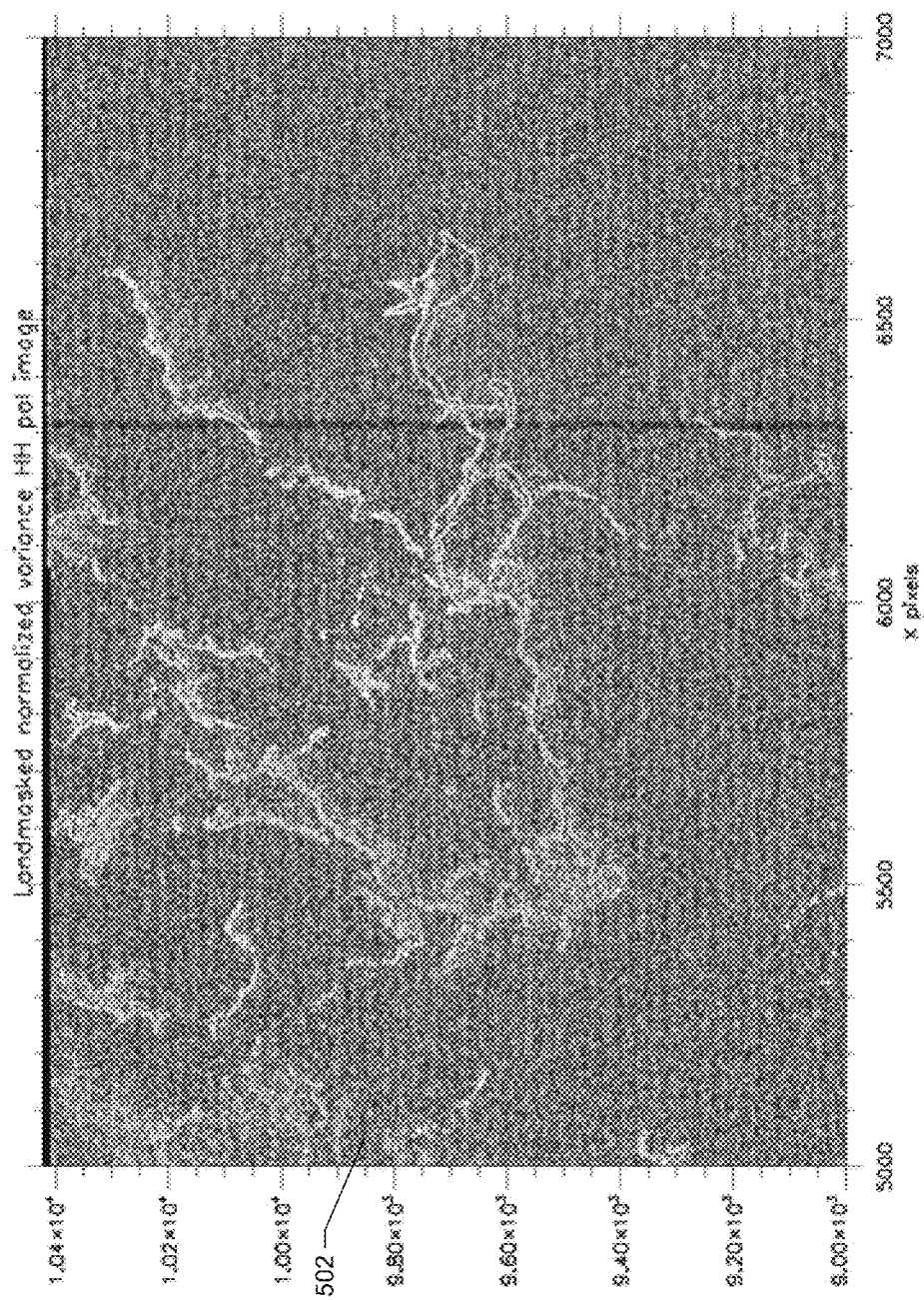
FIGS. 11 and 12 illustrate magnifications of the coefficient of variation thresholding according to an example embodiment.

In an example embodiment, a ratio of the standard deviation to the mean, e.g. a coefficient of variation (COV), may be applied to remove the atmospheric signatures. The COV may additionally enhance the edges of the ice. FIG. 10 illustrates a COV of the radar image 302. The atmospheric signatures are substantially reduced. FIG. 11 illustrates a magnified depiction of the COV for the old ice area 502.

Figure 12:
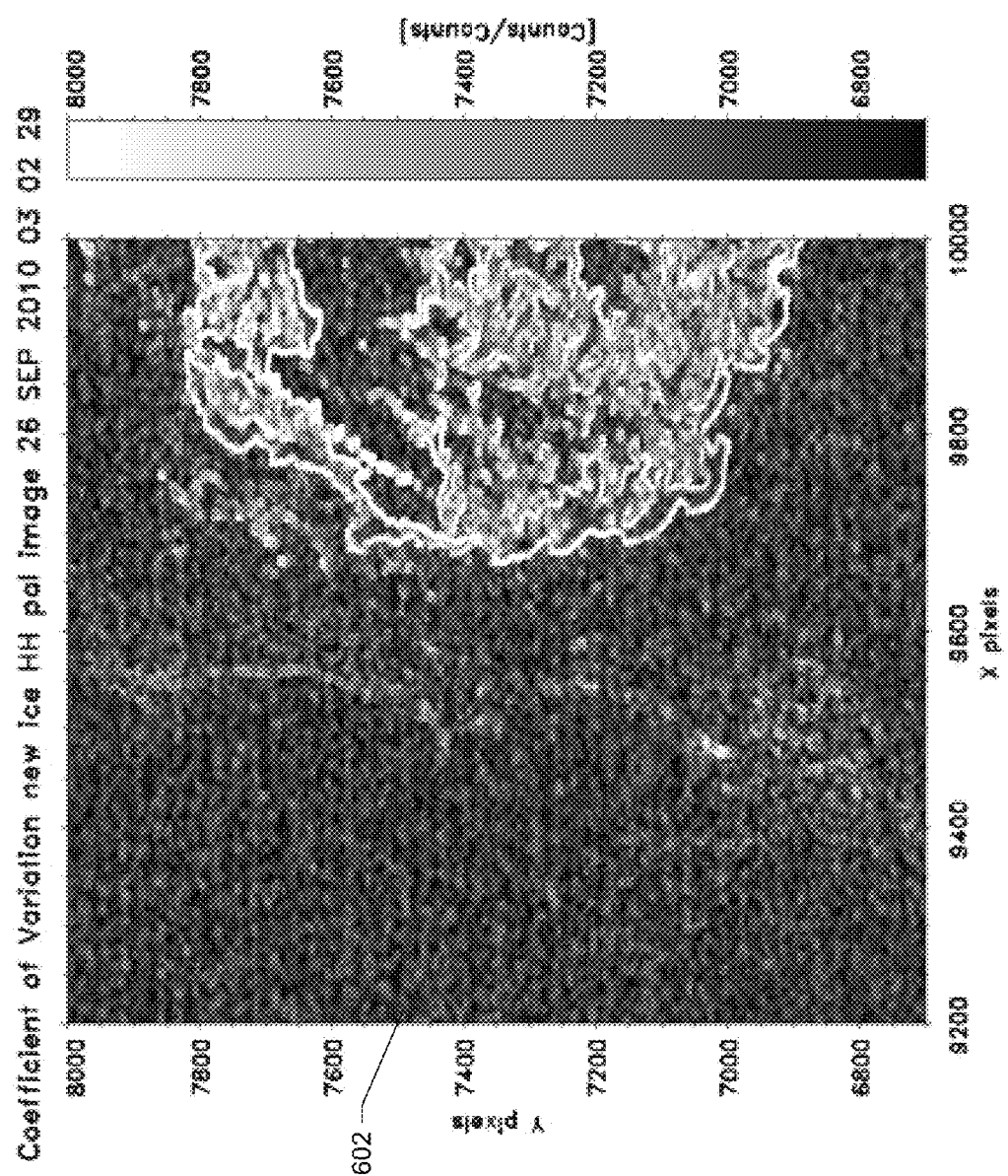

In some example embodiments, the new ice area in the HH polarization radar image COV includes a signature approximately as bright as the multi-year ice next to it as depicted in FIG. 12. A threshold in COV may be used to separate ice and water. In some example embodiments, the threshold in COV may not be universal. In an example embodiment in which the thresholding in COV would not be universal, an adaptive approach may be used to derive the threshold.

Adaptive COV Thresholding

In an example embodiment, an adaptive COV threshold may be applied to a plurality of pixels of the radar image 302. An ice/water mask may be generated for the radar image, e.g. an active ice/water mask based on the COV thresholding. In an example embodiment, the COV threshold for ice and water may be determined from histogram distributions of the COV based on the image composition, e.g. majority water or majority ice. In an instance in which the determined passive polarization ratio ice concentration for the entire radar image 302 was less than 50%, the peak of the COV histogram may be assumed to be from the water pixels. Similar to the passive histograms, the maximum COV for water may be selected where the distribution fell 20 dB below the peak of the histogram, on the high side. In some example embodiments, isolated bright radar pixels from breaking waves, e.g. sea spikes, may appear on the ice side of the COV due to their infrequent occurrence. In an example embodiment, the sea spike radar pixel locations may be cross checked against 0% ice radiometer pixels seaward of the ice edge margin and/or with a spatial density check performed. The cross check of the sea spike radar pixel locations and/or the spatial density check may eliminate most of the false positives due to sea spikes.

In an instance in which the determined passive polarization ratio ice concentration for the radar image 302 was greater than 50%, the peak of the COV histogram may not be from water. In an instance in which the peak of the COV histogram is not from water, the COV threshold may be determined from the maximum COV measured in regions where the passive polarization ratio ice concentrations were zero, and a predetermined margin away from the ice edge.

The pixels of the radar image may be compared to the COV threshold. In some example embodiments, the COV thresholding may act as an edge detector, adding narrow spans back to the ice mask by gap filling. The narrow spans may be added back into the ice mask in an instance in which, the returned power across the gap is greater than a threshold of a local mean plus a predetermined factor, such as 1.45 times the local standard deviation, for either the HH polarization or the HV polarization image. In some example embodiments, narrow spans may be added back into the ice mask in an instance in which the co-located passive pixel associated with the active pixels includes a passive polarization ratio ice concentration greater than a predetermined value, such as about 35%. In an example embodiment, a gap in the ice mask may be determined to be filled in an instance in which the gap is wider than two active pixels. Limiting the size of a gap for filling may prevent the gap-filling from becoming prohibitively computationally intensive.

Figure 13:
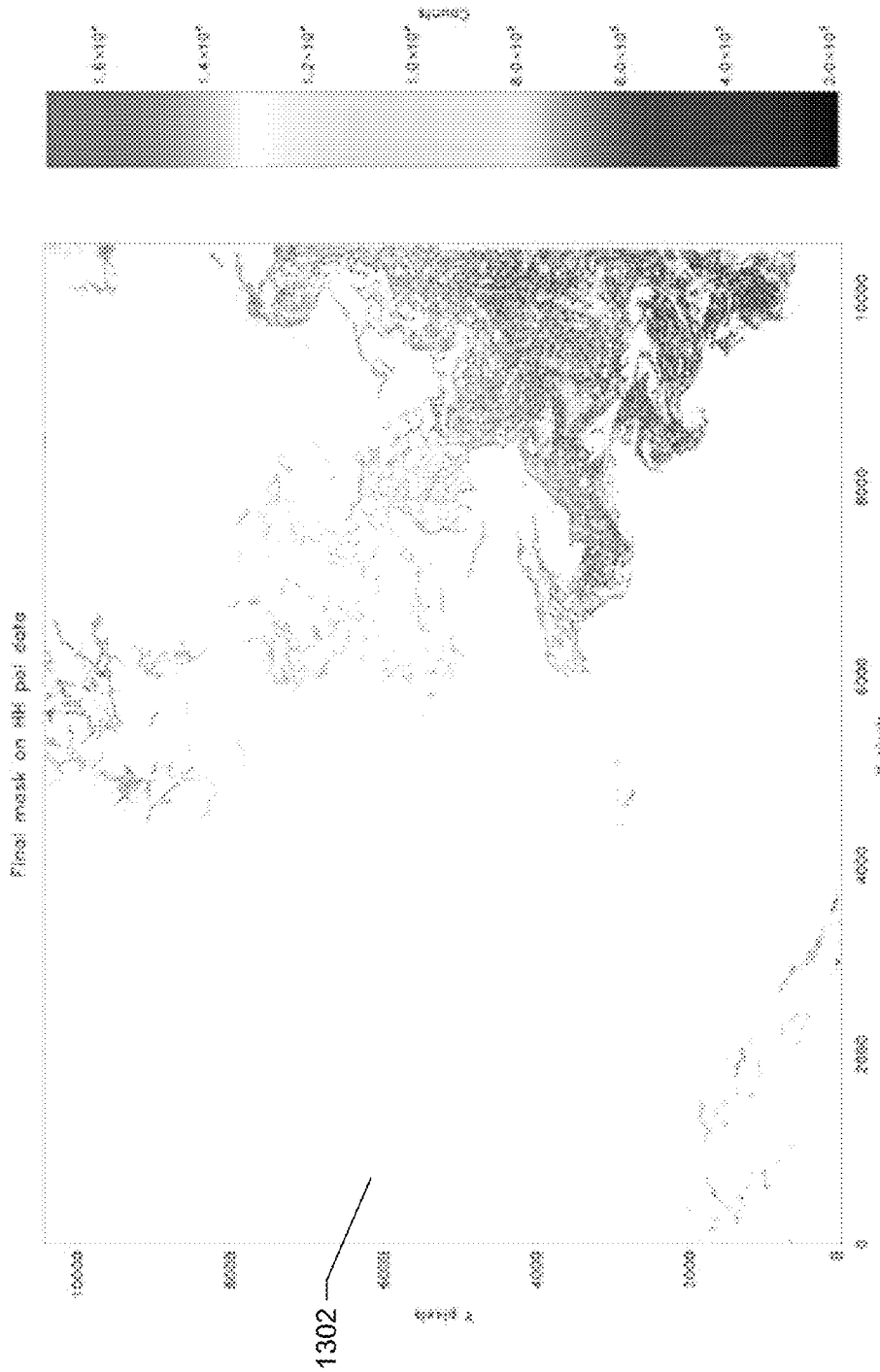
FIG. 13 illustrates an ice typing mask according to an example embodiment.
Figure 14:
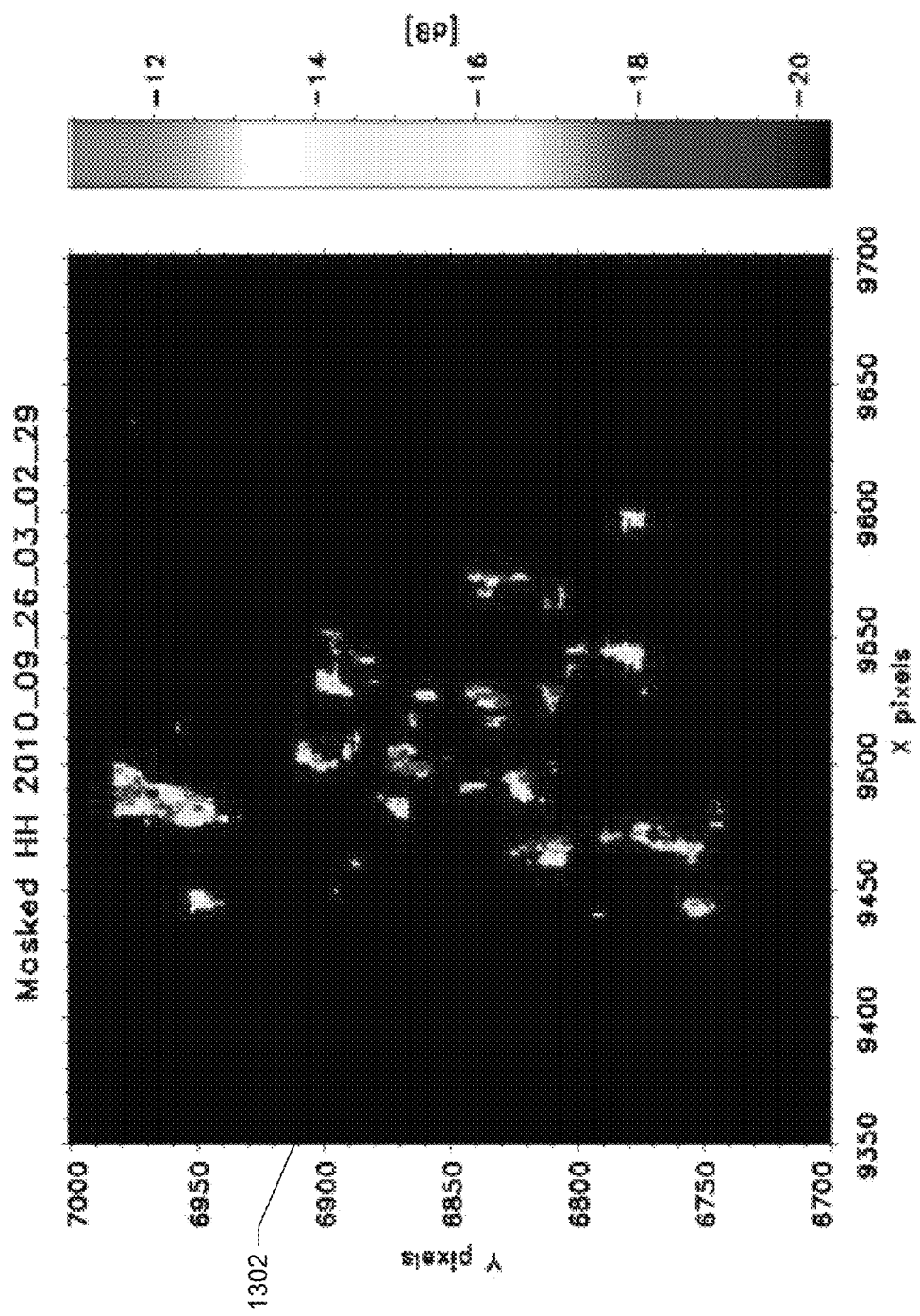
FIG. 14 illustrates a magnification of the ice typing mask according to example embodiments.

FIG. 13 illustrates a final ice/water mask 1302 for the radar image 302 after adaptive COV thresholding and gap filing. Water and land have been colored white and ice has been colored for visibility. FIG. 14 illustrates a magnification of the ice/water mask in the new ice area 602. The raw counts of the ice have been logged in dB and colored to clarity against a black mask.

In an example embodiment, the ice/water mask for land fringe pixels may be generated by a separate adaptive COV thresholding. A second adaptive COV thresholding may be applied over the land fringe pixels, with an altered set of ice/water separation rules that use the COV masks for HH polarization and HV polarization of the radar image only. Further, the ice gap filling search is narrowed to between 2 and 40 pixels, rather than the two pixel minimum, discussed above. The gap filling search may be altered due to ice tending to form, initially, into strips parallel to the coast, until ice growth filled the entire land fringe area with ice.

Merging the Passive and Active Ice/Water Masks

FIGS. 15 and 16 illustrate the HH polarization and HV polarization of a second example radar image 1502, respectfully. The radar image 1502 captured includes the Chukchi Sea on Oct. 28, 2010. Although atmospheric signatures are mostly absent in this active image 1502, the ice present is mostly new and young, with a small percentage of multi-year and thick first-year in some sections, according to the regional ice chart from Canadian Ice Service (CIS). In the upper right is a high concentration of young ice 1506, exhibiting the variability in cross section due to the presence or absence of frost flowers, as discussed above. Along the coast, new ice is depicted forming and thickening to young ice in patches. A broad new ice region 1508 is growing in the lower left, with some strands thickening to the young stage. In new ice region 1508, the HH polarization radar image 1502 shows clearly the new ice, while the HV polarization radar image 1502 with reduced cross section and reduced SNR is more sensitive to the rising cross section of the young ice 1506.

In an example embodiment, the COV masks for the HH polarization and HV polarization radar image 1502 may be combined. The combined COV masks for the HH polarization and HV polarization radar images 1502 may provide discrimination between ice and water. In the upper right portion of the HH polarization and HV polarization radar images 1502 of the present example, are responding only to the changes in surface roughness, except at the edge, where the open water and wave action around the floes limited hyper-cooling of atmospheric water vapor and frost flower formation.

The passive polarization ratio ice concentration mask may be insensitive to the surface effects from the frost flowers, since the penetration depth for 6 GHz is on the order of 30 cm. A passive polarization ratio threshold may be set to merge the high concentration of ice pack into the final ice/water mask. In an example embodiment, the passive polarization ratio may be a high ice concentration such as 70%, 75%, 85%, or the like. Pixels which satisfy the passive polarization ratio threshold, e.g. are greater than or equal to the passive polarization ratio threshold may be classified as ice in the ice/water mask. The remaining pixels may be tagged as water.

Figure 17:
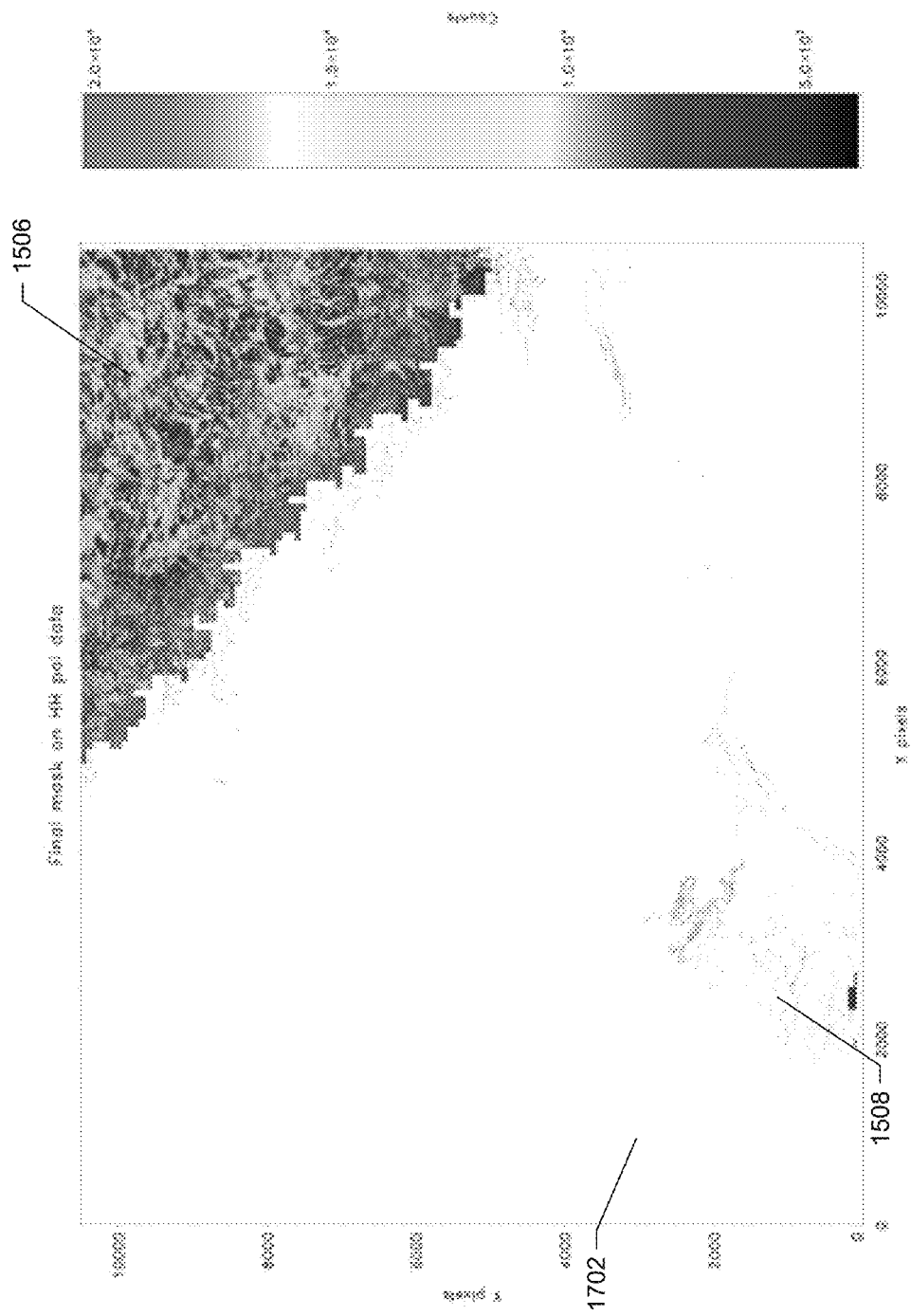
FIGS. 17 and 18 illustrate an ice typing mask for the second dual polarization radar image according to an example embodiment.
Figure 18:
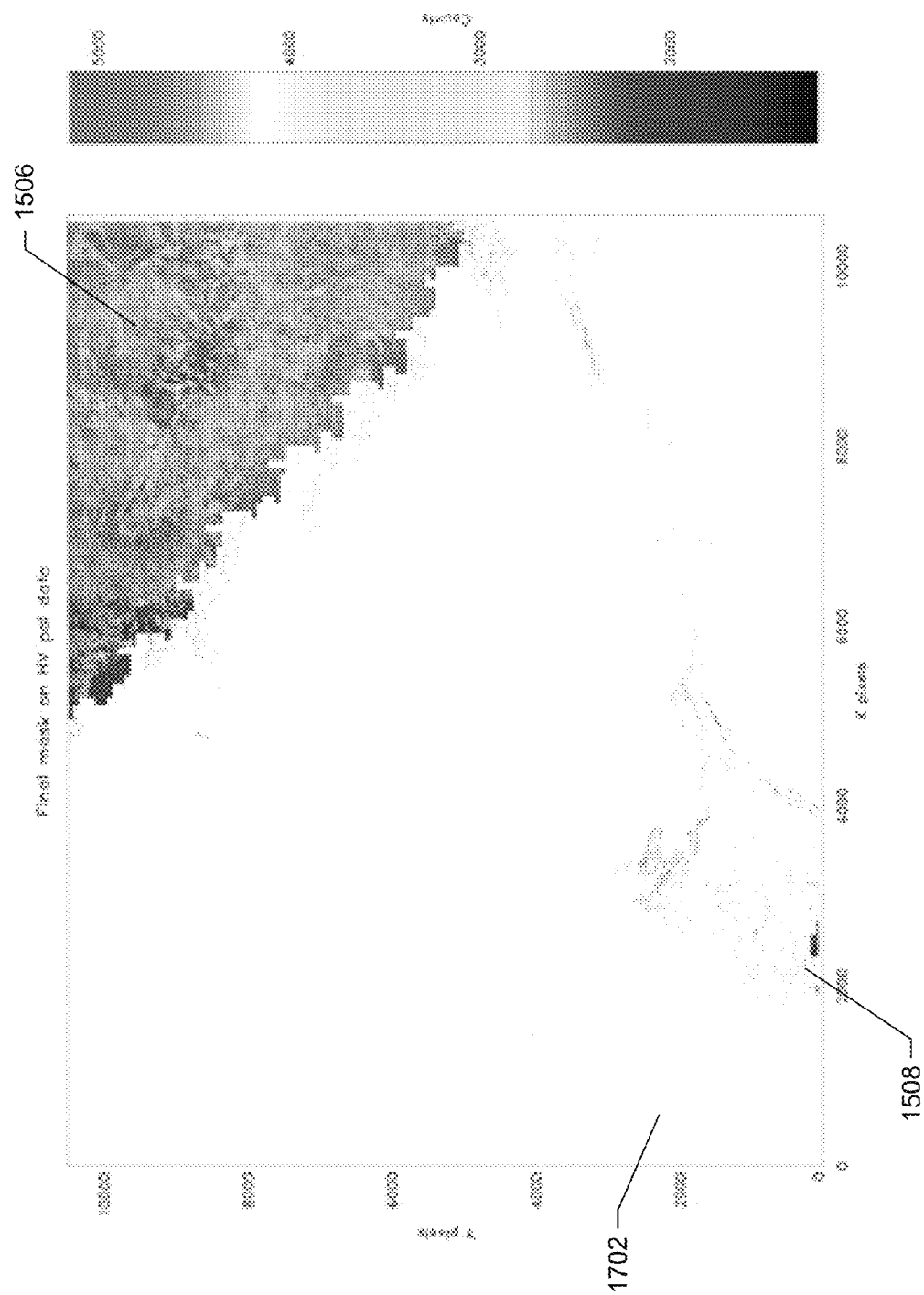

FIGS. 17 and 18 illustrate a final typing ice mask 1702 for the HH polarization and HV polarization active images. The land and water pixels have been colored white and the ice pixels have been colored for visibility. The predominantly new/young ice mix is mostly missed in the land fringe search of a radiometer image, but may be reacquired by examining HH and HV coefficients of variation of the radar image 1502. An example of the importance of including all four channels, e.g. HH polarization and HV polarization active images and the H and V polarization radiometer images, in the ice typing mask is evident in the lower left of the image, e.g. new ice region 1508 where the passive channels could not be used in the land fringe.

Example Ice Typing

Ice typing data may be received from a database, such as the database server 42. The ice typing data may include calibrated cross sections and brightness temperatures for frequencies ranging from 1-90 GHz for use in setting the ice typing ranges. Calibrated radar cross sections and brightness temperatures for ice typing may be acquired from spacecraft, aircraft, helicopter, or ground-based active and passive RF sensors for each ice seasons, from early freeze-up to late melt. In an example embodiment in which the passive RF data is reported in emissivity, rather than brightness temperature, emissivity may be converted to brightness temperature by multiplying the measured values by surface temperatures. The emissivity may be converted to brightness temperature due to relatively small emissivity changes at 6 GHz, especially for thicker ice types from freeze-up through early melt.

In an example embodiment, the ice typing data may include polarimetric measurements, such as C-band polarimetric measurements, for multiple ice types. In some example embodiments, the polarimetric measurements may be modeled and measured HH polarization and HV polarization cross sections as a function of snow thickness. One example ice typing data polarization measurement indicated that 16 cm thick snow reduced cross sections on the order of 5 dB below that of snow-free ice. This change due to snow may be on the order of changes due to incident angle across most of the active images, and may be factored in when setting cross section ranges for ice typing.

The ice typing data may include brightness temperature ranges for ice types. Calibrated measurements may be used to determine the brightness temperature ranges. Table 1 shows example ice typing data including radar cross section and brightness temperature ranges for freeze-up and late melt stage. The values for the early freeze-up period were used for the Chukchi Sea example above discussed in reference to FIGS. 15-18 and the late melt values were used for the Beaufort Sea example discussed above in reference to FIGS. 3-14.

TABLE 1

| RF Channel by Season | Range for Ice Type [low/high] | | | |
|---|---|---|---|---|
| | New | Young | First Year | Multi-Year |
| $\sigma^0_{HH}$ [dB] | | | | |
| Freeze-up | −24.3/−12.5 | −30.5/−5.8 | −23.0/−19.0 | −20.0/−8.1 |
| Late melt | −30.5/−22.2 | −20.0/−16.0 | −28.2/−22.1 | −21.0/−6.5 |
| $\sigma^0_{HV}$ [dB] | | | | |
| Freeze-up | −32.0/−25.5 | −39.0/−17.7 | −32.0/−28.0 | −28.4/−10.0 |
| Late melt | −32.5/−27.6 | −27.0/−25.0 | −27.9/−16.5 | −27.9/−16.5 |
| $T_BH$ [K] | | | | |
| Freeze-up | 85.0/100.0 | 176.7/223.6 | 113.1/200.4 | 133.1/200.4 |
| Late melt | 73.2/82.8 | 83.9/88.2 | 77.9/96.2 | 92.3/133.1 |
| $T_BV$ [K] | | | | |
| Freeze-up | 170.8/181.9 | 194.0/251.1 | 200.4/207.6 | 200.4/207.6 |
| Late melt | 143.8/164.4 | 154.3/164.3 | 155.6/165.5 | 168.4/207.6 |

The ice typing data may be applied to the each ice pixel of the horizontal polarization and the vertical polarization channels of the radiometer image and the HH and HV channels of the radar image. Each ice pixel may be tagged or labeled new ice, young ice, first year ice, or multi year ice based on the brightness temperature and/or radar cross section of the ice pixel.

As discussed above in reference to applying the land mask, ice typing in the land fringe and for areas where the passive ice concentrations are less than a predetermined value, such as 15%, may be performed on the radar image 302, 1502, and not performed on the radiometer image. The ice typing in the land fringe and low passive polarization ratio ice concentrations may reduce contamination of self-emissions of open water in the radiometer image. In an instance in which the passive polarization ratio ice concentration drops to or below the predetermined value, an ice type signature seen in the relatively large land area, e.g. 26×26 km, pixels may be indistinguishable from the self-emissions of the open ocean.

In an instance in which the cross sections and/or brightness temperatures associated with a given ice pixel do not all fall into range for the same ice type and/or if there is disagreement between the HH polarization radar image, HV polarization radar image and/or H polarization radiometer image and V polarization radiometer image of the ice characterization, then the ice pixel may be tagged as mixed. In an example embodiment, mixed ice may be the correct designation, because the radar image 302, 1502 pixel land area may be larger than a football field, therefore ice types may not be uniform over the land area associated with the ice pixel of that size.

Ice Concentration Determination

In an example embodiment, an ice concentration may be determined based on the tagged pixels. Each pixel in the radar image may be tagged as land, coast, water, or ice of one of the four unique types, or the one mixed type. The ice concentration may be determined by calculating a summation. A total ice concentration $I_c$ over a radar image 302, 1502 may be the number of ice pixels $P_I$ in the ice/water mask divided by the number of ice pixels plus water pixels $P_W$ in the image times 100, for expression as a percentage.
$I_c = P_I / P_{I+} P_W$
By including only the water and land pixels the calculation accounts for the existence of the land and coast pixels.

Calculating ice concentration may also be performed in subareas. In an example embodiment, the ice and water pixels may be grouped into subareas of ten radar image pixels by ten radar image pixels. In an example embodiment, in which the radar image is SCANSAR wide RADARSAT data, the land area associate with the subgroup may be 1 km by 1 km. Total ice concentration in a subarea may be the number of ice pixels divided by the number of ice pixels and water pixels in the subarea.

Examples and Comparison with NIC Ice Charts and CIS Ice Analyses

Figure 19:
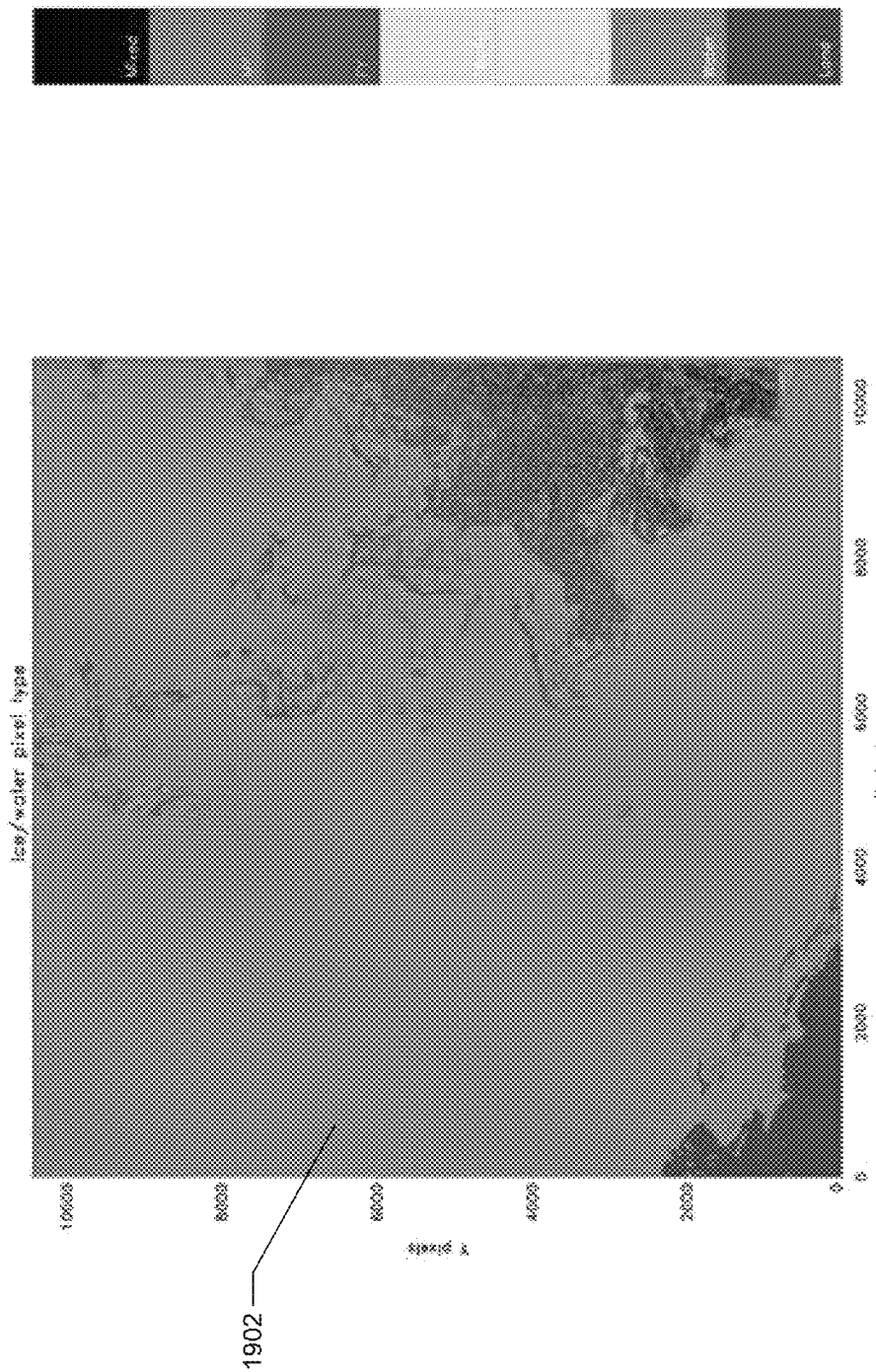
FIG. 19 illustrates an example ice typing according to an example embodiment.
Figure 20:
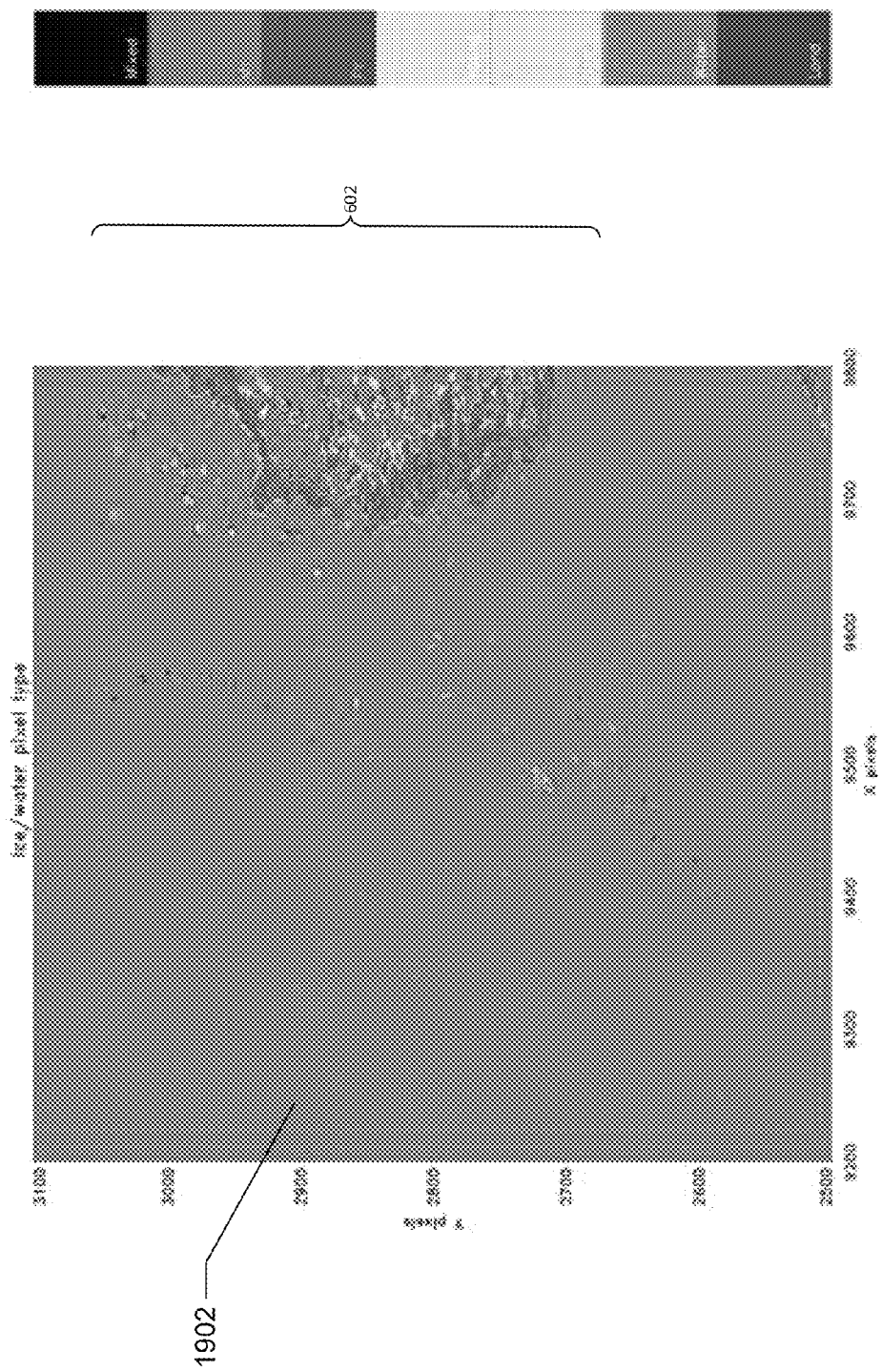
FIGS. 20 and 21 illustrate magnifications of the ice typing according to an example embodiment.
Figure 21:
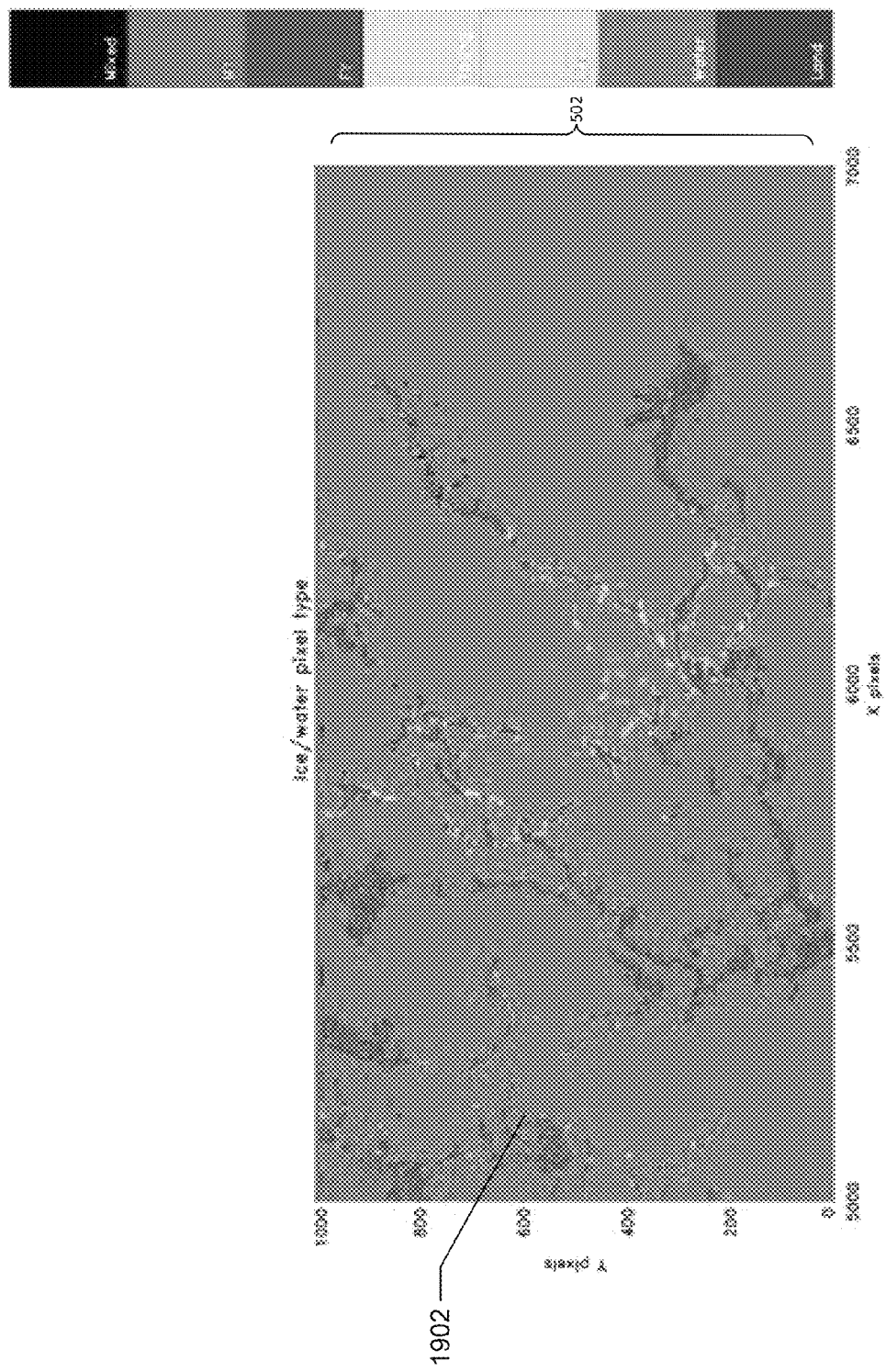
Figure 22:
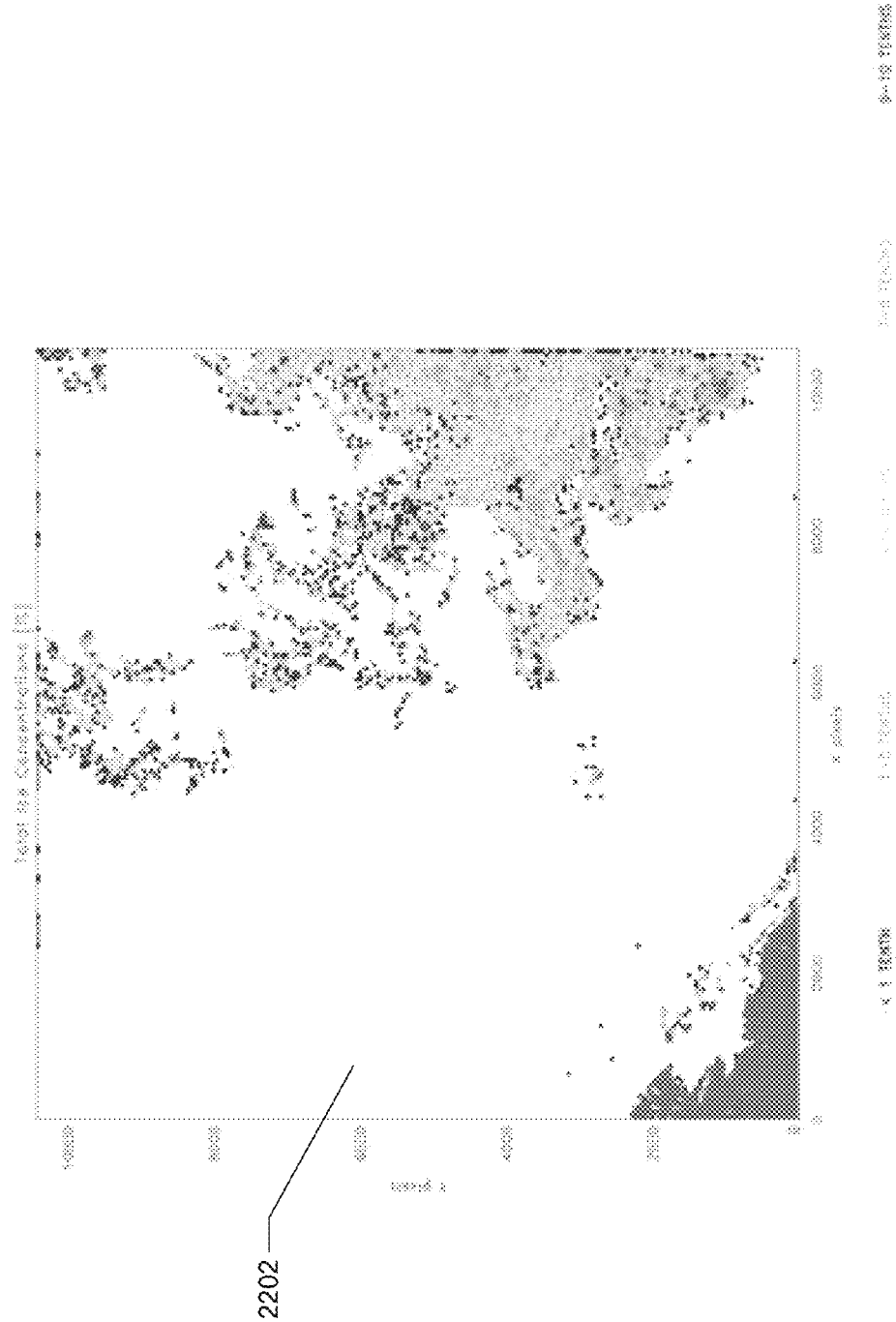
FIG. 22 illustrates a total ice concentration according to an example embodiment.
Figure 23:
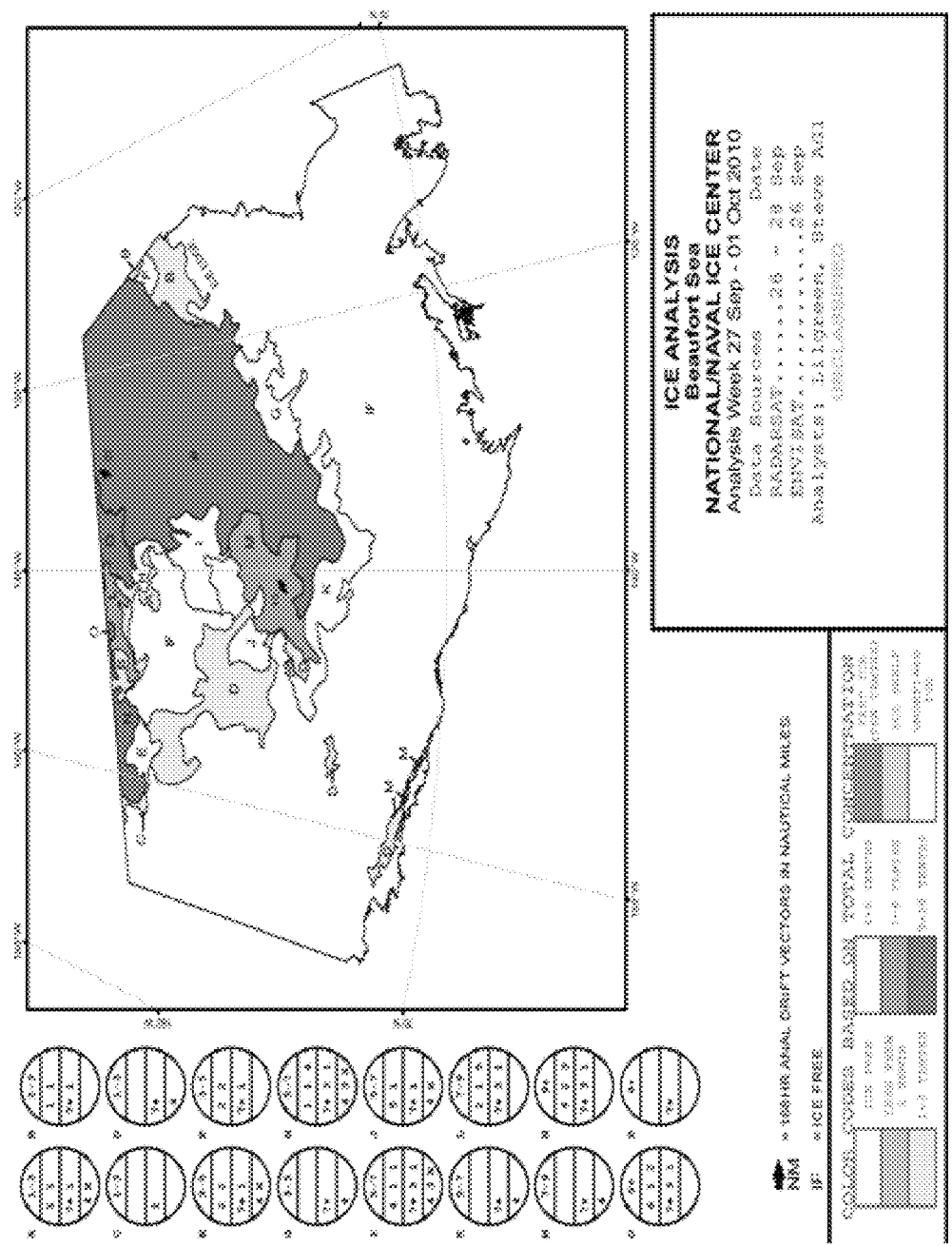
FIGS. 23 and 24 illustrate ice concentration charts according to an example embodiment.
Figure 24:
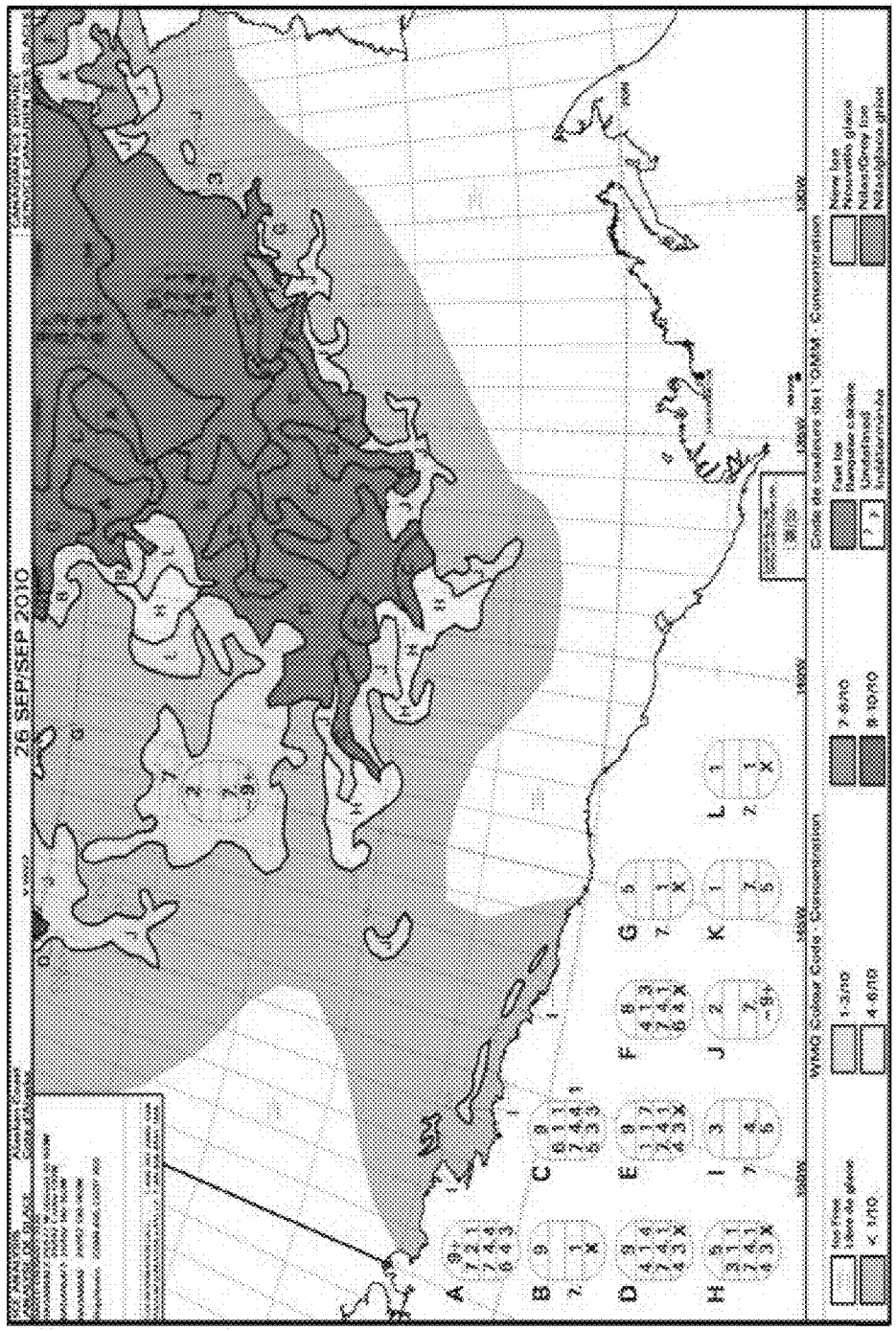
Figure 25:
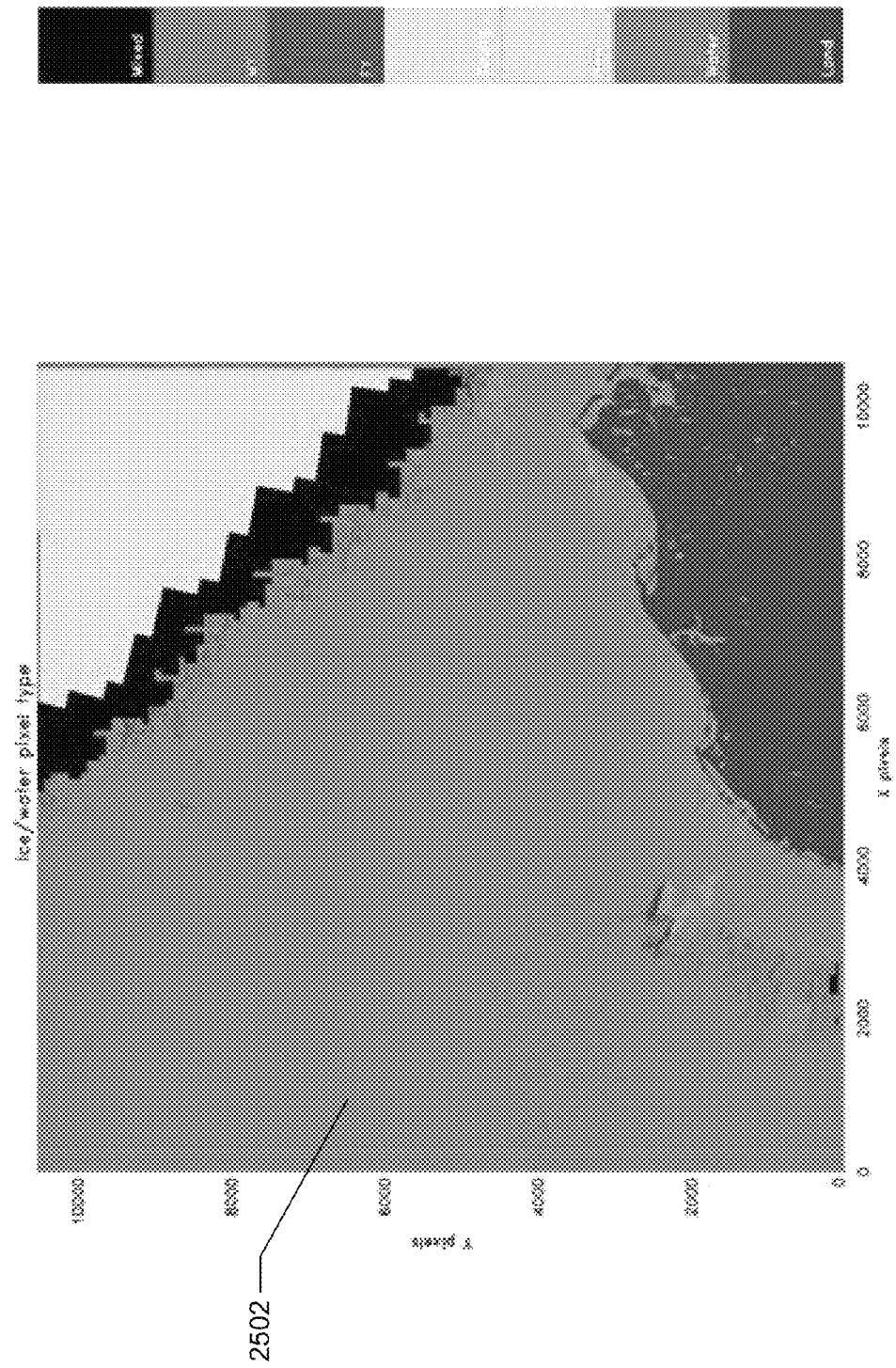
FIG. 25 illustrates an ice typing according to an example embodiment.
Figure 26:
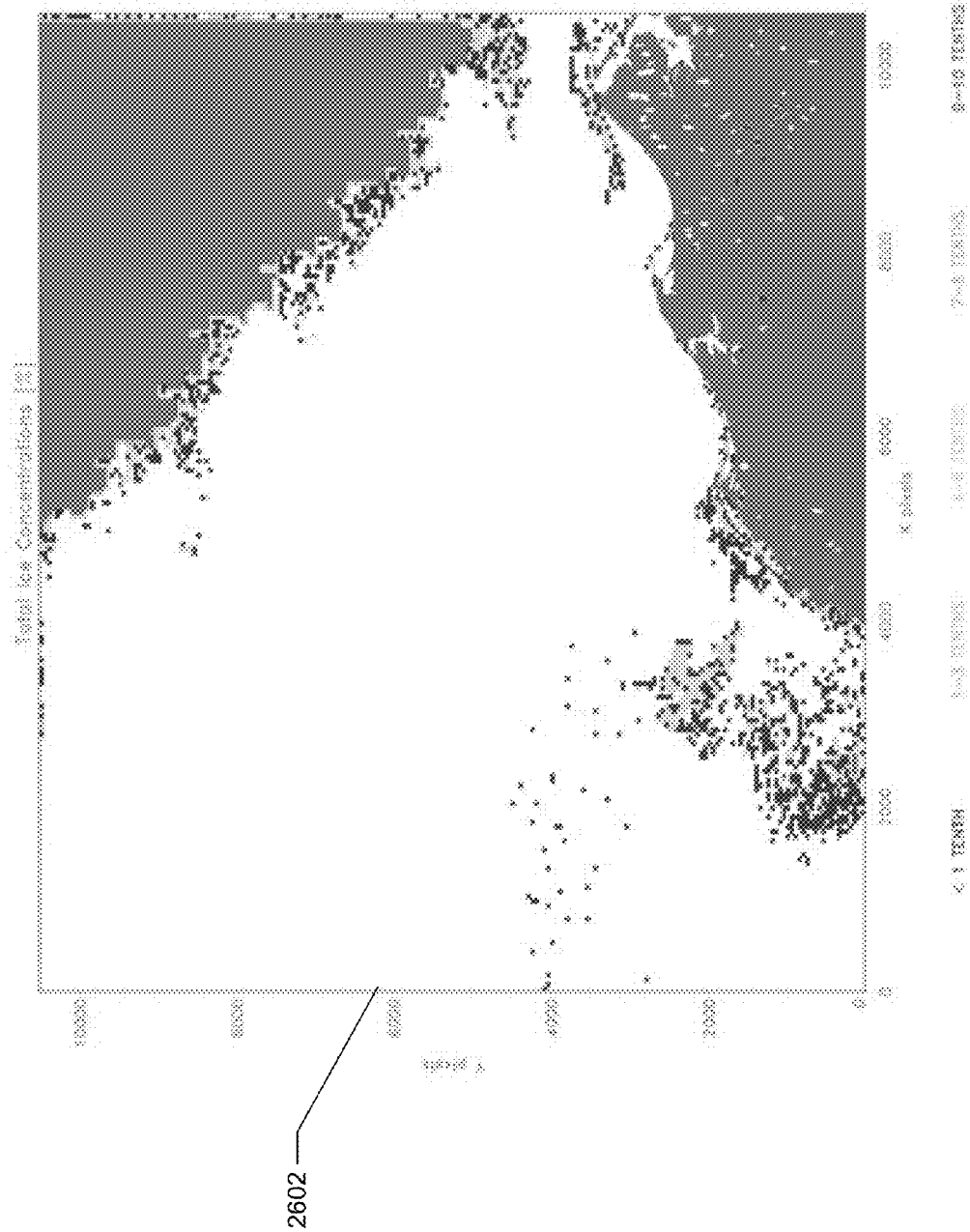
FIG. 26 illustrates a total ice concentration according to an example embodiment.
Figure 27:
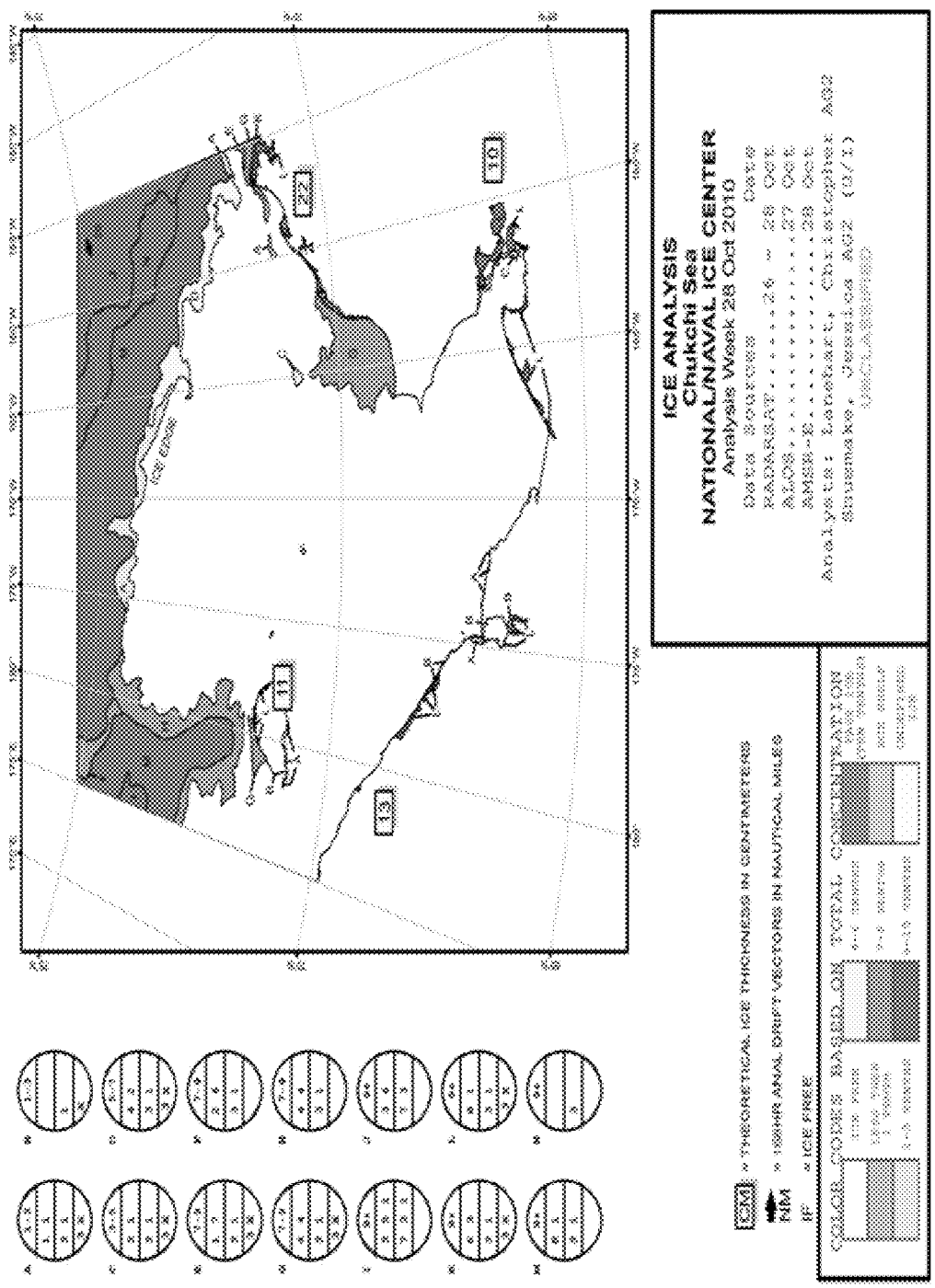
FIGS. 27 and 28 illustrate example ice concentration charts according to an example embodiment.
Figure 28:
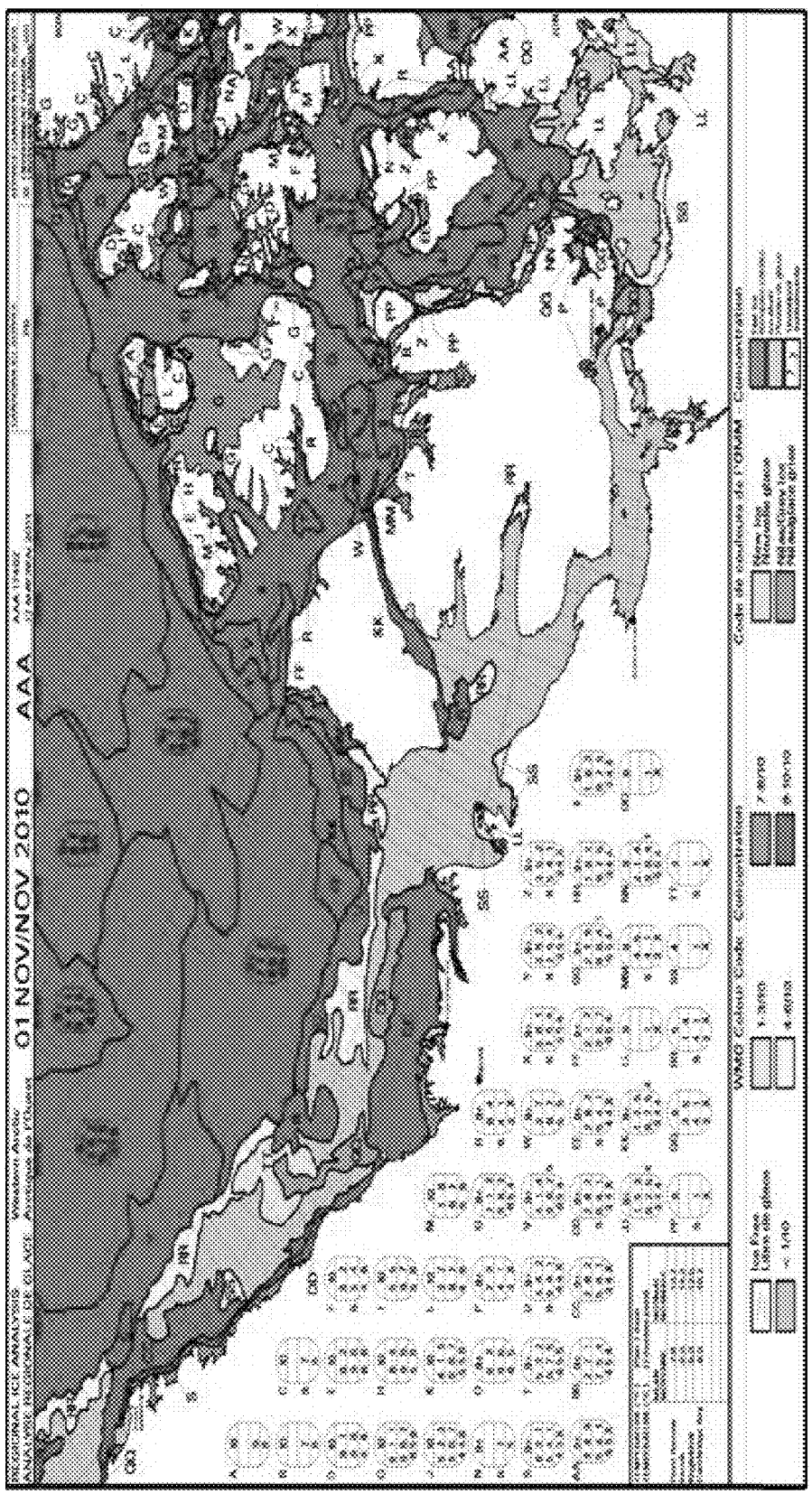

Ice typing 1902 for the Beaufort Sea example as discussed in reference to in FIGS. 3-14 is depicted in FIG. 19. Total ice concentration 2202 for the Beaufort Sea example as discussed in reference to in FIGS. 3-14 is depicted in FIG. 22. Water is depicted as white, land is depicted as dark grey in the lower left corner and the ice concentrations are colored for tenths. FIG. 20 depicts a magnification of the ice typing 1902 for the new ice area 602, and FIG. 21 depicts a magnification of the ice typing 1902 for the old ice area 502. The Naval/National Ice Center (NIC) chart for the Beaufort Sea for Analysis Week 27 Sep.-1 Oct. 2010, which is based in part on the Beaufort Sea example of Sep. 28, 2010 radar image is illustrated in FIG. 23. The CIS daily chart, FIG. 24, shows the area around the RADARSAT radar image. Ice concentrations for the operational charts are reported as tenths in two-tenths ranges, and areas of similar total and partial concentrations and ice types are grouped into areas labeled with World Meteorological Organization (WMO) Egg Codes. FIGS. 25-28 depict the equivalent charts for the Chukchi Sea example captured on Oct. 28, 2010, with the exception that the CIS charts are regional Western Arctic Charts and not specific to the Chukchi Sea. FIG. 25 shows the ice typing 2502, FIG. 26 depicts the total ice concentrations 2602, FIG. 27 is the NIC chart, and FIG. 28 is the CIS chart.

The ice detection algorithm in the analysis of the Beaufort radar image tends to label pixels on the boundaries of multi-year ice areas as young ice, due to the overlap in cross section and brightness temperature ranges. The CIS chart carries some partial concentrations of thick first-year ice that neither the NIC chart nor the ice detection algorithm detect which may be due to the reliance of manual analyses on continuity—the rule of thumb that thicker forms of ice seen in previous analyses are assumed to continue to be present if ice drifting is not sufficient to move ice out of an area in thicker ice pack—whereas the ice detection algorithm does not account for such a continuity. For the Example Chukchi sea radar image, the ice detection algorithm fails to pick up all the new/young ice present in the land fringe (area G on the NIC chart in FIG. 27), because the radiometer channels are not useable there. Active cross-polarization ratios may be utilized to correct this deficiency, as well as detect and eliminate the sea spike signatures near area G that have survived passive pixel identification and the spatial density check.

Example Distributed Graph Processing Flow Chart

Figure 29:
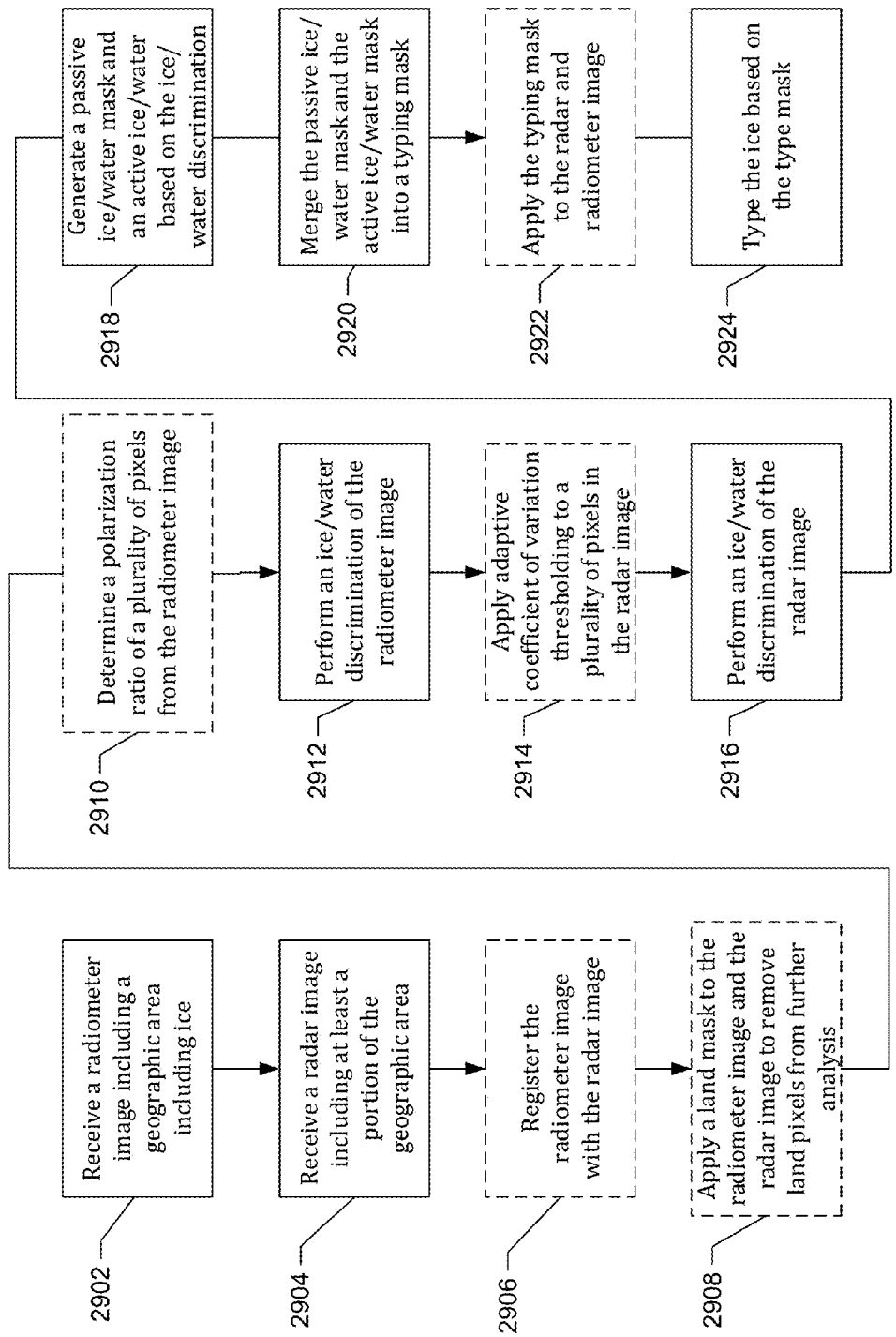
FIG. 29 illustrates a method for ice analysis according to an example embodiment.

From a technical perspective, the ice analyzer module 44 described above may be used to support some or all of the operations described above. As such, the apparatus described in FIG. 2 may be used to facilitate the implementation of several computer program and/or network communication based interactions. As such, the platform described in FIG. 2 may be used to facilitate the implementation of several computer program and/or network communication based interactions. As an example, FIG. 29 is a flowchart of a method and program product according to an example embodiment of the invention. It will be understood that each block of the flowchart, and combinations of blocks in the flowchart, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory device of a user terminal (e.g., client 20, application server 40, and/or the like) and executed by a processor in the user terminal. As will be appreciated, any such computer program instructions may be loaded onto a computer or other programmable apparatus (e.g., hardware) to produce a machine, such that the instructions which execute on the computer or other programmable apparatus create means for implementing the functions specified in the flowchart block(s). These computer program instructions may also be stored in a computer-readable memory that may direct a computer or other programmable apparatus to function in a particular manner, such that the instructions stored in the computer-readable memory produce an article of manufacture which implements the functions specified in the flowchart block(s). The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In this regard, a method according to one embodiment of the invention is shown in FIG. 29. The method may be employed for ice analysis based on radar and radiometer images. The method may include, receiving a radiometer image including a geographic area including ice, at operation 2902. The method may also include receiving a radar image including at least a portion of the geographic area, at operation 2904. At operation 2912, the method may include performing an ice/water discrimination of the radiometer image. The method may include performing an ice/water discrimination of the radar image at operation 2916. The method may include generating a passive ice/water mask and an active ice/water mask based on the ice/water discrimination, at operation 2918, merging the passive ice/water mask and the active ice/water mask into a typing mask, at operation 2920, and typing the ice based on the typing mask, at operation 2924.

In an example embodiment, the method may optionally include, as denoted by the dashed box, registering the radiometer image with the radar image, at operation 2906. The method may optionally include applying a land mask to the radiometer image and the radar image to remove land pixels from further analysis, at operation 2908, and determining a polarization ratio of a plurality of pixels of the radiometer image, at operation 2910. The method, at operation 2914, may include applying the adaptive coefficient of variation thresholds to the radar image. The method may optionally include applying adaptive coefficient of variation thresholding to the active ice/water mask, at operation 2914. At operation 2920, the method may optionally include applying the typing mask to the radar and radiometer image.

In an example embodiment, an apparatus for performing the method of FIG. 29 above may comprise a processor (e.g., the processor 52) or processing circuitry configured to perform some or each of the operations (2902-2924) described above. The processor may, for example, be configured to perform the operations (2902-2924) by performing hardware implemented logical functions, executing stored instructions, or executing algorithms for performing each of the operations. In some embodiments, the processor or processing circuitry may be further configured for additional operations or optional modifications to operations 2902-2924. In this regard, for example in an example embodiment, the typing the ice includes determining if the ice is multi-year ice, first year ice, young ice, or new ice based on a brightness temperature and normalized radar cross section of the typing mask. In an example embodiment, the processing circuitry is further configured to apply a land mask to the radiometer image and the radar image to remove land pixels from further analysis. In some embodiments, the processing circuitry is further configured to register the radiometer image with the radar image, and the merging of the passive ice/water mask with the active ice/water mask is based on the registering of the radiometer image with the radar image. In an example embodiment, the processing circuitry is further configured to apply adaptive coefficient of variation thresholding to the active ice/water mask. In some embodiments, the radiometer image and the radar image are captured by radars operating in C band. In an example embodiment, the ice/water discrimination includes determining a polarization ratio of a plurality of pixels of the radiometer image and a coefficient of variation of a plurality of pixels of the radar image. The ice/water discrimination is based on the polarization ratio of respective pixels of the plurality of pixels of the radiometer image and the coefficient of variation of respective pixels of the plurality of pixels of the radar image. In some embodiments, the radiometer image and the radar image are captured by RF systems operating with dual polarization. In an example embodiment, the dual polarization comprises horizontal transmission-vertical receive (HV) and horizontal transmit-horizontal receive (HH) for the radar image and horizontally-polarized (H) and vertically-polarized (V) radiometer image. In some embodiments, the radiometer image and the radar image are captured contemporaneously or near contemporaneously.

Many modifications and other embodiments of the measuring device set forth herein will come to mind to one skilled in the art to which these inventions pertain having the benefit of the teachings presented in the foregoing descriptions and the associated drawings. Therefore, it is to be understood that the measuring devices are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. An ice analyzer comprising processing circuitry configured to:
   receive a radiometer image including a geographic area including ice;
   receive a radar image including at least a portion of the geographic area;
   perform ice/water discrimination of the radiometer image and the radar image;
   generate a passive ice/water mask and an active ice/water mask based on the ice/water discrimination;
   merge the passive ice/water mask and the active ice/water mask into a typing mask; and
   type the ice based on the typing mask.

2. The ice analyzer of claim 1, wherein typing the ice comprises:
   determining if the ice is multi-year ice, first year ice, young ice, or new ice based on a brightness temperature and normalized radar cross section of the typing mask.

3. The ice analyzer of claim 1, wherein the processing circuitry is further configured to:
   apply a land mask to the radiometer image and the radar image to remove land pixels from further analysis.

4. The ice analyzer of claim 1, wherein the processing circuitry is further configured to:

register the radiometer image with the radar image, and
wherein merging of the passive ice/water mask with the active ice/water mask is based on registering of the radiometer image with the radar image.

5. The ice analyzer of claim 1, wherein the processing circuitry is further configured to:
apply adaptive coefficient of variation thresholding to the radar image.

6. The ice analyzer of claim 1, wherein the radiometer image and the radar image are captured by RF systems operating in C band.

7. The ice analyzer of claim 1, wherein the ice/water discrimination comprises:
determining a polarization ratio of a plurality of pixels of the radiometer image and a coefficient of variation of a plurality of pixels of the radar image,
wherein the ice/water discrimination is based on the polarization ratio of respective pixels of the plurality of pixels of the radiometer image.

8. The ice analyzer of claim 7, wherein the radiometer image and the radar image are captured by RF systems operating with dual polarization.

9. The ice analyzer of claim 8, wherein the dual polarization comprises horizontal transmit-vertical receive (HV) and horizontal transmit-horizontal receive (HH) for the radar image and horizontally-polarized (H) and vertically-polarized (V) for the radiometer image.

10. The ice analyzer of claim 1, wherein the radiometer image and the radar image are captured contemporaneously or near contemporaneously.

11. An method of analyzing ice comprising:
receiving a radiometer image including a geographic area including ice;
receiving a radar image including at least a portion of the geographic area;
performing ice/water discrimination of the radiometer image and the radar image;
generating a passive ice/water mask and an active ice/water mask based on the ice/water discrimination;
merging, using processing circuitry, the passive ice/water mask and the active ice/water mask into a typing mask; and
typing, using processing circuitry, the ice based on the typing mask.

12. The method of claim 11, wherein typing the ice comprises:
determining if the ice is multi-year ice, first year ice, young ice, or new ice based on a brightness temperature and normalized radar cross section of the typing mask.

13. The method of claim 11 further comprising:
applying a land mask to the radiometer image and the radar image to remove land pixels from further analysis.

14. The method of claim 11, further comprising:
registering the radiometer image with the radar image, and
wherein merging of the passive ice/water mask with the active ice/water mask is based on registering of the radiometer image with the radar image.

15. The method of claim 11, further comprising:
applying adaptive coefficient of variation thresholding to the radar image.

16. The method of claim 11, wherein the radiometer image and the radar image are captured by RF systems operating in C band.

17. The method of claim 11, wherein the ice/water discrimination comprises:
determining a polarization ratio of a plurality of pixels of the radiometer image and a plurality of pixels of the radar image,
wherein the ice/water discrimination is based on the polarization ratio of respective pixels of the plurality of pixels of the radiometer image and on the coefficient of variation of respective pixels of the plurality of pixels of the radar image.

18. The method of claim 17, wherein the radiometer image and the radar image are captured by RF systems operating with dual polarization.

19. The method of claim 18, wherein the dual polarization comprises horizontal transmit-vertical receive (HV) and horizontal transmit-horizontal receive (HH) for the radar image and horizontally-polarized (H) and vertically-polarized (V) for the radiometer image.

20. The method of claim 11, wherein the radiometer image and the radar image are captured contemporaneously or near contemporaneously.

* * * * *